(12) United States Patent
Khoury et al.

(10) Patent No.: US 11,058,721 B2
(45) Date of Patent: Jul. 13, 2021

(54) COMPOSITION COMPRISING A SUBSTANTIALLY PURE POPULATION OF MULTIPOTENT STROMAL CELLS ENCAPSULATED IN PLATELET-POOR PLASMA (PPP)

(71) Applicants: CELLS FOR CELLS S.A., Las Condes Santiago (CL); UNIVERSIDAD DE LOS ANDES, Santiago (CL)

(72) Inventors: Maroun Khoury, Las Condes Santiago (CL); Claudia Brizuela, Santiago (CL); Ioannis Angelopoulos, Santiago (CL)

( * ) Notice: Subject to any disclaimer, the term of this patent is extended or adjusted under 35 U.S.C. 154(b) by 155 days.

(21) Appl. No.: 16/478,002

(22) PCT Filed: Jan. 15, 2018

(86) PCT No.: PCT/IB2018/050243
§ 371 (c)(1),
(2) Date: Jul. 15, 2019

(87) PCT Pub. No.: WO2018/131003
PCT Pub. Date: Jul. 19, 2018

(65) Prior Publication Data
US 2019/0365804 A1    Dec. 5, 2019

(30) Foreign Application Priority Data

Jan. 16, 2017   (EP) ..................... 17151688

(51) Int. Cl.
| | | |
|---|---|---|
| A61K 35/28 | (2015.01) | |
| A61K 35/16 | (2015.01) | |
| A61K 35/51 | (2015.01) | |

(52) U.S. Cl.
CPC ............ *A61K 35/16* (2013.01); *A61K 35/28* (2013.01); *A61K 35/51* (2013.01)

(58) Field of Classification Search
None
See application file for complete search history.

(56) References Cited

U.S. PATENT DOCUMENTS

| | | | |
|---|---|---|---|
| 8,920,791 B2 * | 12/2014 | Nakashima | ............ A61P 43/00 424/93.7 |
| 2018/0303878 A1 | 10/2018 | Khoury et al. | |
| 2018/0304502 A1 | 10/2018 | Acevedo et al. | |
| 2019/0038675 A1 | 2/2019 | Khoury et al. | |
| 2019/0194460 A1 | 6/2019 | Enrione Cáceres et al. | |

OTHER PUBLICATIONS de la Puente et al., "Cell culture in autologous fibrin scaffolds for applications in tissue engineering," *Experimental Cell Research* 322:1-11, 2014.
Kim et al., "Fibrin Glue Improves the Therapeutic Effect of MSCs by Sustaining Survival and Paracrine Function," *Tissue Engineering: Part A* 19(21-22):2373-2381, 2013.
Martinez et al., "Platelet Poor Plasma and Platelet Rich Plasma Stimulate Bone Lineage Differentiation in Periodontal Ligament Stem Cells," *Journal of Periodontology*, 14 pages, 2015.
Muraglia et al., "Combined platelet and plasma derivatives enhance proliferation of stem/progenitor cells maintaining their differentiation potential," *Cytotherapy* 17: 1793-1806, 2015.
Park et al., "In vitro and in vivo osteogenesis of human mesenchymal stem cells derived from skin, bone marrow and dental follicle tissues," *Differentiation* 83:249-259, 2012.
Saoud et al., "Regeneration and Repair in Endodontics—A Special Issue of the Regenerative Endodontics—A New Era in Clinical Endodontics," *Dentistry Journal* 4(3):1-15, 2016.

\* cited by examiner

*Primary Examiner* — Qiuwen Mi
(74) *Attorney, Agent, or Firm* — Seed IP Law Group LLP

(57) ABSTRACT

The present invention relates to a root canal filler and a dental tissue regeneration method by using the root canal filler.

7 Claims, 20 Drawing Sheets

E

F

D

E

A

B

C

B

C

D

E

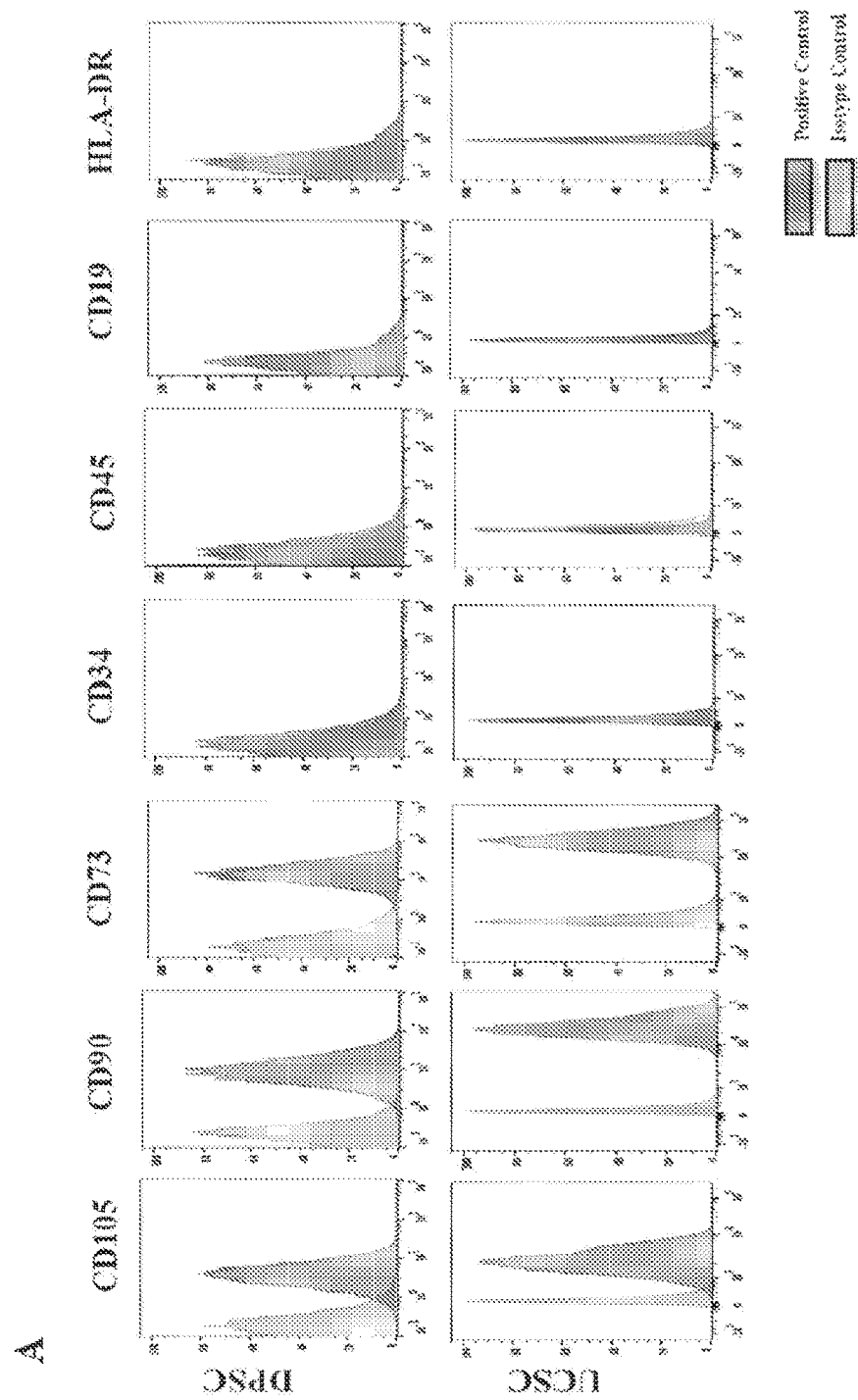

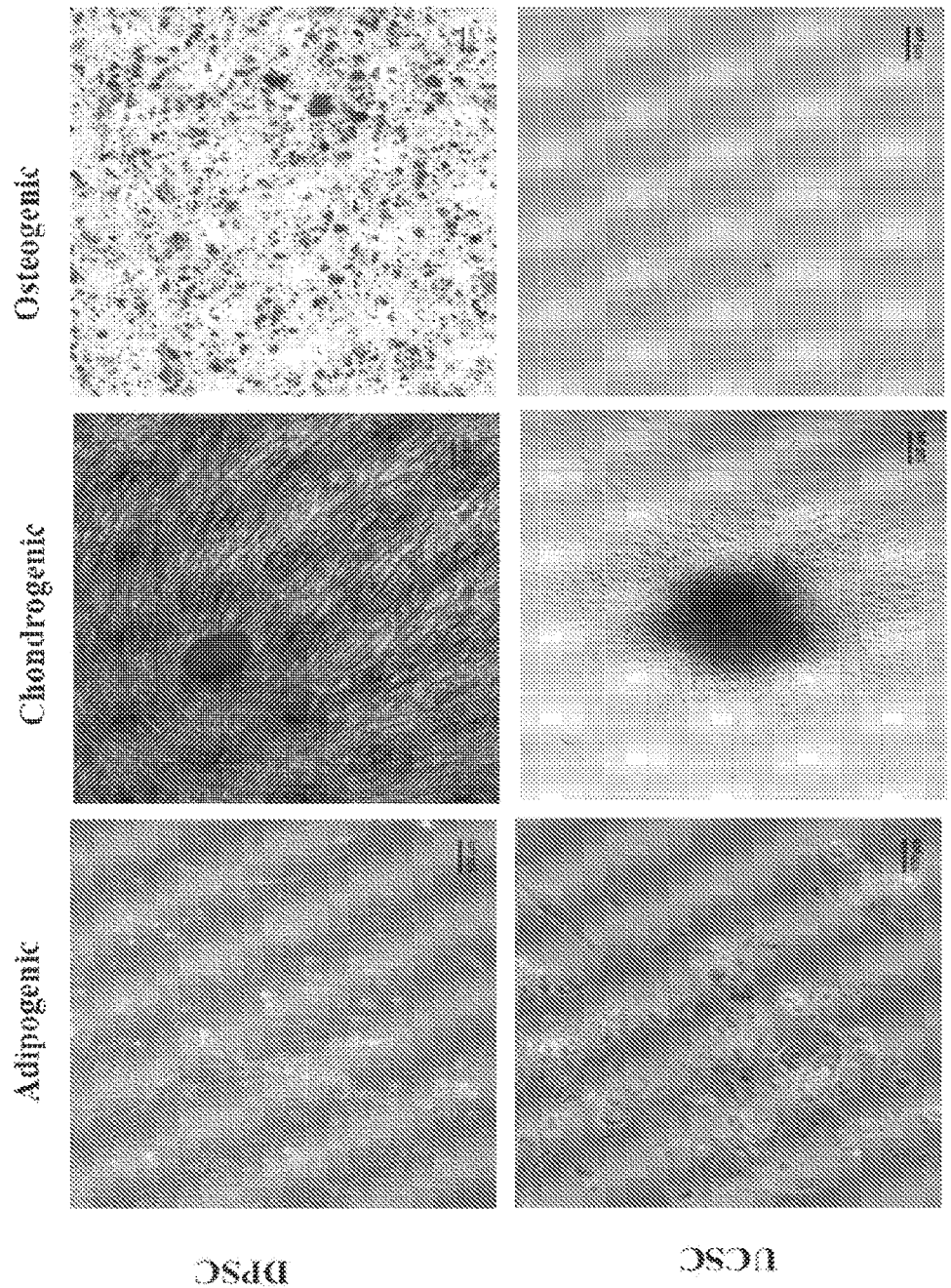

COMPOSITION COMPRISING A SUBSTANTIALLY PURE POPULATION OF MULTIPOTENT STROMAL CELLS ENCAPSULATED IN PLATELET-POOR PLASMA (PPP)

TECHNICAL FIELD OF THE INVENTION

The present invention relates to a root canal filler and a dental tissue regeneration method by using the root canal filler.

BACKGROUND OF THE INVENTION

When dental caries is deep enough to reach dental pulp, pulpectomy is usually performed for treatment of the caries. However, the dental pulp not only has a function to block external stimulus by reparative dentin formation, but also functions to inhibit further invasion of bacterial by sense and prevent tooth fracture caused by chewing a hard material with the sense of occlusion. In addition, the dental pulp can maintain protein and water in dentin by metabolism, and additionally keep the tensile strength and other properties of dentin. The dental pulp is also known to have an infection defence mechanism by immune system.

NiTi alloy rotary files are used popularly in endodontics, because of morphological complexity of the root canal. However, complete pulpectomy, enlargement of root canal and root canal filling are almost impossible. Thus, pulpectomy often leads to periapical periodontitis, and has high possibility of resultant loss of the tooth. In addition, most of the reports on pulp regeneration in the emptied root canal are those in immature teeth. In the case of deep caries with pulpitis or periapical periodontitis in mature teeth with complete apical closure, no method or root canal filler for dental tissue regeneration have been developed yet. There is thus an unmet need for development of a method to preserve the dental pulp as long as possible for longevity of teeth.

In this sense, mesenchymal stem cells (MSC) hold great promise in the dental regeneration field. They could be derived from a large variety of sources such as the bone marrow (BM), the adipose tissue, the dental pulp, the gingival tissue or the umbilical cord and placenta. MSCs are pluripotent cells and have the ability to differentiate into different types of cells (osteogenic, chondrogenic and adipogenic). Despite the various sources of MSCs, bone marrow-MSCs have been predominantly used extensively for cell therapy, however, one of the major drawbacks of using bone marrow derive MSCs (BM-MSCs) is the yield, which is relatively low, therefore harvesting a large volume of BM-MSCs is difficult. In this sense, according to different studies, in order to perform a clinical trial a large number of cells are required sharing a stable phenotype in order to obtain successful results. This objective is difficult to achieve with BM-MSCs.

On the other hand, at the present moment five different human dental stem cells have been isolated and characterized: dental pulp stem cells (DPSCs), stem cells from exfoliated deciduous teeth (SHED), periodontal ligament stem cells (PDLSCs), stem cells from apical papilla (SCAP), and dental follicle progenitor cells (DFPCs). Placental MSCs (P-MSCs) have been obtained from multiple placental areas including both maternal and foetal origins as well as from the umbilical cord blood (UCB), amniotic fluids, amniotic membrane, Wharton's jelly, chorionic membrane, chorionic villi and decidua. The most common placental source for MSCs in clinical trials is the umbilical cord, more precisely the UCB. Clinical reports have showed that UCB-MSCs transplantation in patients with decompensated liver cirrhosis is safe and improve the patient's quality of life. However, it has been shown that MSCs are present at a very low frequency in the UCB which represents a limitation for their application at a higher scale.

Furthermore, Platelet-Poor Plasma (PPP) is blood plasma with very low number of platelets ($<10 \times 10^3/\mu L$). Traditionally, PPP was recommended for use in platelet aggregation studies to both adjust the Platelet-rich plasma concentration, and to serve as a control. PPP may have elevated levels of fibrinogen, which has the ability to form a fibrin-rich clot once activated. Wound healing requires cell migration and attachment, which is facilitated by this fibrin clot Methods to prepare PPP are well known in the art, in this sense, an exemplary methodology is as follows:

Within 2 hours of blood collection, centrifuge capped citrate tube for 15 minutes at an RCF (relative centrifugal force) of 3000-3500 g;

Using a plastic transfer pipet, remove the top ¾ of plasma and place it in a plastic centrifuge tube with cap;

Centrifuge the plasma (in the plastic centrifuge tube) for another 15 minutes at 3000-3500 g;

Using a plastic transfer pipet, remove the top ¾ into a plastic tube. Do not disturb the plasma in the bottom of the spun tube, where any residual platelets will be;

Aliquots with visible red cells or hemolysis (pink plasma) are not acceptable; and Freeze plasma immediately. Samples for most laboratory assays should be frozen within 4 hours of collection.

Plasma-derived fractions have been used as source of growth factors; however, limited knowledge concerning their biologic effects and cytocompatibility have limited their application as supporting scaffold.

We herein show that the combination of MSCs and PPP, MSCs encapsulated in PPP, synergistically increases the regeneration potential in endodontic conditions thus providing an alternative useful treatment method to preserve the dental pulp as long as possible for longevity of teeth.

BRIEF DESCRIPTION OF THE INVENTION

An object of the present invention, which was made to solve the problems above, is to provide a novel and creative root canal filler for regeneration of dental tissue by filling a scaffold into the root canal of a mature tooth with complete apical closure after pulpectomy and a dental tissue regeneration method by using such a root canal filler. Said root canal filler is made of mesenchymal stem cells (MSCs) encapsulated or grown in Platelet-Poor Plasma. In particular, the present invention describes that there is a significant increase in the number of cells after 12 days of implantation compared to day 1 (pre-implantation) as shown in FIGS. 2 (E), (F) and (G) of MSCs encapsulated in PPP. The present invention thus indicates the usefulness of PPP as a support and vehicle for MSCs, in particular for the preparation of a root canal filler for the regeneration of dental tissue, in particular for the generation of pulp.

BRIEF DESCRIPTION OF THE FIGURES

FIG. 9. (A) Both cell sources (UC-MSC and DPSC) showed a positive expression of the common MSC markers such as CD105, CD90, CD73, CD34, CD45, CD19 and HLA-DR and (B) also DPSC and UC-MSC were induced to differentiate into mesodermal tissues (adipopogenic, chondrogenic and osteogenic) lineages.

DESCRIPTION

Figure 1:
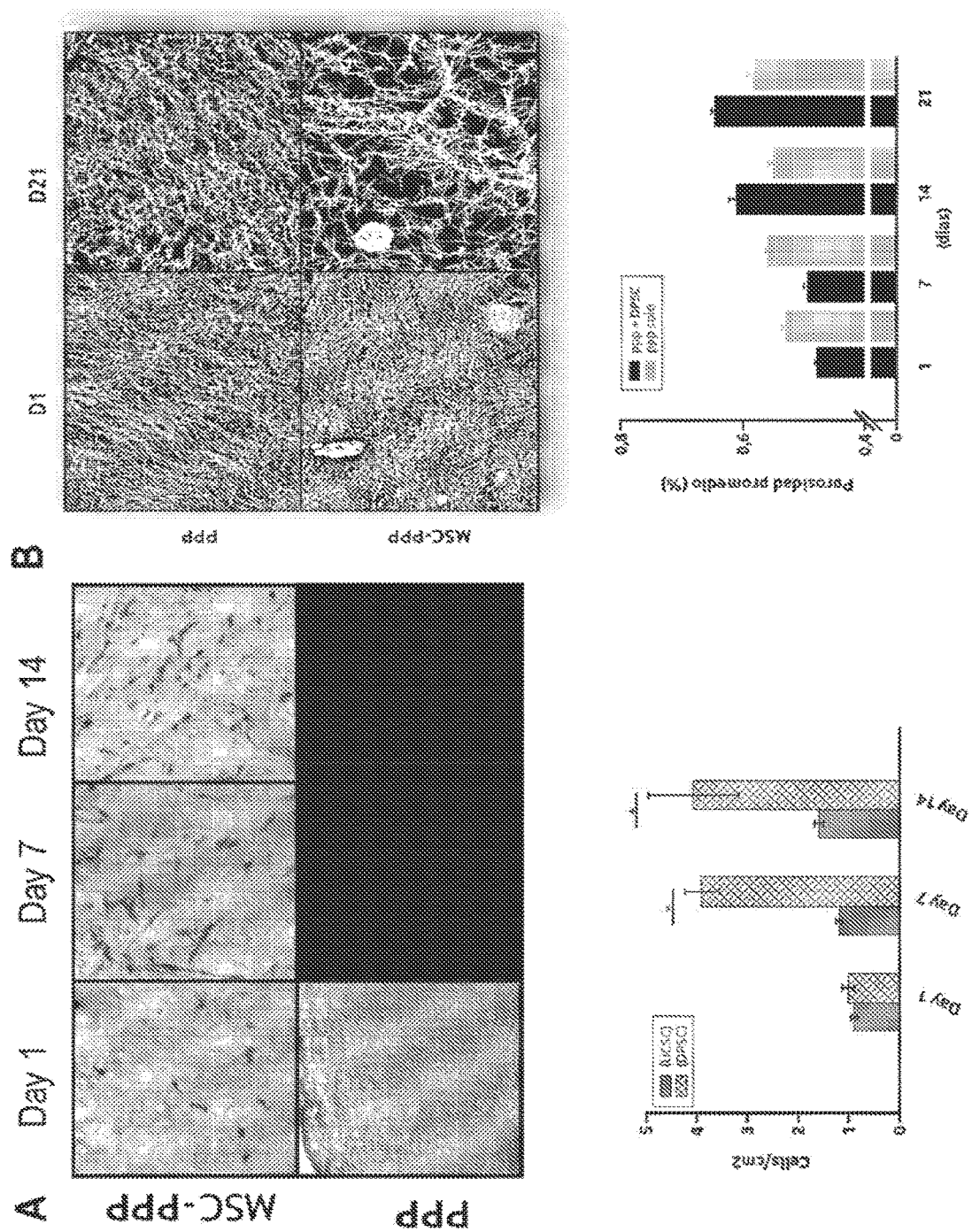
FIG. 1. (A) Histology of MSCs grown in PPP for 1, 7 and 14 days. Cells were then counted and compared among the two different sources MSCs (mesenchymal stem cells) (UC-MSCs (umbilical cord stem cells) and DPSCs (dental pulp stem cells)). (B) Electron microscopy analysis (EM) of PPP with or without cultured MSCs and day 1 or 21 post-culture showing porosity changes.

Hereinafter, favourable embodiments of the present invention will be described specifically with reference to attached figures.

Embodiment 1

The invention in the present embodiment relates to a dental tissue regeneration method for regeneration of dental tissue in root canal, characterized by injecting a population of multipotent stromal cells encapsulated in Platelet-Poor Plasma (PPP) into the apical side of the root canal after pulpectomy or enlargement and cleaning of an infected root canal. The dental tissues to be regenerated are, for example, blood vessel, nerve, dental pulp, dentin and others in root canal. In the invention in the present embodiment after pulpectomy or enlargement and cleaning of an infected root canal, the dental pulp is removed and disinfected; the apical portion of the root is cut out open (apicoectomized); and a root canal filler is transplanted. In the invention in the present embodiment, a synthetic filler or blood clot is not transplanted into the disinfected hollow root canal, but a scaffold superior in biocompatibility without causing adverse effects and in low immunogenicity with multipotent stromal cells, which mimics dental pulp tissue, is used. The root canal filler is preferably filled to ¼ to ⅔ of the apical part of the root canal, more preferably ⅓ of the apical part.

Hereinafter, the dental tissue regeneration method in embodiment 1 will be described with reference to the figures and examples. As shown in the examples, an extracellular matrix is prepared, in particular PPP. The extracellular matrix is the so-called scaffold, a matrix for cell attachment.

As shown in the examples, the root canal filler is prepared by growing or encapsulating multipotent stromal cells including dental pulp stem cells or umbilical cord stem cells in the extracellular matrix (PPP). The cells including dental pulp stem cells are attached to the apical part of the root canal of the root canal filler. A typical example of the method of producing the root canal filler is provided in the examples.

In this sense, for example, a tooth with pulpitis is subjected to extract in the dental tissue regeneration method in the present embodiment. The targeted tooth is then subjected to pulpectomy. The targeted tooth is a tooth in which microbial infection reaches the coronal pulp or the radicular pulp because of caries, pulpitis etc. Pulpectomy is an operation to remove the whole dental pulp present in the tooth.

After pulpectomy, it is desirable to adjust the size of the apical foramen to a particular width, by enlargement of the root canal of the targeted tooth. As will be described below, it is because it is easier to fill the root canal filler in fixing the root canal filler in the root canal after pulpectomy and blood vessel and nerve penetrate therein easily from the apical periodontal tissue, if the root canal is enlarged.

For example, the width of the apical foramen, i.e., the diameter of root canal, is desirably 0.7 mm or more and 1.5 mm or less. When the width of the root canal is less than 0.7 mm, blood vessel and nerve do not penetrate easily from the apical periodontal tissue, and it may be difficult to fill the root canal filler, while when the width of the root canal is more than 1.5 mm, enlargement of the root canal may lead to application of a load more than needed on the targeted tooth, thus causing tooth fracture.

After pulpectomy of the targeted tooth, the root canal filler (a composition comprising a population of multipotent stromal cells encapsulated in Platelet-Poor Plasma (PPP)) is inserted into the apical side of the root canal for example with tweezers. Such composition might be injected for example with Pipetman or syringe.

The cells included in the composition may be the autologous cells extracted from the animal subjected to the treatment for dental tissue regeneration or the allogeneic cells extracted from an animal different from the animal subjected to the treatment for dental tissue regeneration. In this sense, the multipotent stromal cells or mesenchymal stem cells (MSC) useful in the present invention could be derived from a large variety of sources such as the bone marrow (BM), the adipose tissue, the dental pulp, the gingival tissue or the umbilical cord and placenta. MSCs are multipotent cells and have the ability to differentiate into different types of cells (osteogenic, chondrogenic and adipogenic). In particular, MSCs especially useful in the present invention are different human dental stem cells such as: dental pulp stem cells (DPSCs), stem cells from exfoliated deciduous teeth (SHED), periodontal ligament stem cells (PDLSCs), stem cells from apical papilla (SCAP), and dental follicle progenitor cells (DFPCs). In addition, other MSCs useful to carry out the present invention are Placental MSCs (P-MSCs) obtained from multiple placental areas including both maternal and foetal origins as well as from the umbilical cord blood (UCB), amniotic fluids, amniotic membrane, Wharton's jelly, chorionic membrane, chorionic villi and decidua.

The content of the MSCs in the root canal filler is preferably $1 \times 10^3$ cell/µl or more and $1 \times 10^7$ cell/µl or less. It is because a stem cell content of less than $1 \times 10^3$ cell/µl may lead to insufficient regeneration of the dental tissue in root canal. On the other hand, a dental pulp stem cell content of more than $1 \times 10^6$ cell/µl, in particular more than $1 \times 10^7$ cell/µl may cause unexpected adverse reactions to the targeted tooth.

After injection of the root canal filler into the apical side of the root canal, gelatin may be injected to the region above the root canal filler and the root canal is capped with a resin. Then, the extracted tooth is replanted into the odontectomized cavity.

In this way, the dental tissue in the root canal is regenerated. The regenerated dental tissues are, for example, blood vessel and dental pulp tissue in the root canal. Then, the resin is removed once; a morphogen such as BMP or a growth/differentiation factor is applied on the tooth-crown dental pulp; and the root canal is capped with the resin. Dentin is also regenerated, when the morphogen or the growth/differentiation factor is applied on the tooth-crown dental pulp. Tissues that can be regenerated are not limited thereto, and nerve regeneration is also accelerated.

The targeted tooth is a tooth in which microbial infection reaches coronal pulp or radicular pulp because of caries, pulpitis, etc. in embodiment 1 described above, but it is not limited thereto, and the targeted teeth also include a tooth of which the sense of occlusion is weakened by deterioration in nerve function. It is possible in such a case to improve the occlusion sense by regenerating the dental pulp, by injecting a root canal filler after pulpectomy. The targeted teeth also include a tooth in which microbial infection reaches apical periodontal tissue (tooth in which microbes reach the dental pulp and additionally to dentin of root canal wall and apical periodontal tissue).

FURTHER EMBODIMENTS OF THE INVENTION

A second embodiment of the invention refers to a composition comprising a population of multipotent stromal cells encapsulated in Platelet-Poor Plasma (PPP), wherein preferably the population of multipotent stromal cells are selected from the group consisting of dental pulp stem cells (DPSCs), stem cells from exfoliated deciduous teeth (SHED), periodontal ligament stem cells (PDLSCs), stem cells from apical papilla (SCAP), dental follicle progenitor cells (DFPCs), Placental MSCs (P-MSCs), bone marrow MSCs (mesenchymal stem cells), adipose tissue derived MSCs and umbilical cord blood (UCB) MSCs.

In a preferred embodiment, the population of multipotent stromal cells is able to secrete paracrine factors including extracellular vesicles, cytokines and growth factors, comprising or consisting of VEGF, FGF and or DMP-1. We refer to all these released molecules as the MSC secretome. In a preferred embodiment of the invention, the multipotent stromal cells are encapsulated in a biomaterial scaffold, wherein the growth factors are gradually secreted. So, a preferred embodiment of the invention refers to multipotent stromal cells encapsulated in a biomaterial scaffold, wherein the cells secrete the growth factors which are absorbed by the scaffold which in turn secretes them to the exterior, therefore achieving the liberation of the secreted growth factors to the external medium.

Alternatively, it is possible to culture the multipotent stromal cells without the scaffold, collect the secretome, concentrate it, or isolate specific vesicles/molecules and then directly encapsulate them (the secretome) in the scaffolds.

A third embodiment of the invention refers to a pharmaceutical composition which comprises the composition according to the second embodiment of the invention and optionally a pharmaceutically acceptable carrier/vehicle and one or more excipients.

A fourth embodiment of the invention refers to the pharmaceutical composition of the third embodiment of the invention, for use in therapy or medicine, in particular for use in dental tissue regeneration in a method of regenerating dental tissue, in particular pulp tissue, in a root canal, more particularly the method comprises pulpectomizing or enlarging and cleaning of a root canal infected with periapical disease; injecting the composition according to any of claims 1 to 4, into at least an apical area of the root canal. Preferably, width of the root canal in the apical area is adjusted to a particular size, by enlargement of the root canal before insertion of the composition into the apical area of the root canal.

Preferably the concentration of the multipotent stromal cells of any of the above mentioned compositions is from $1 \times 10^3$ cells/µl to $1 \times 10^7$ cells/µl, more preferably about $1 \times 10^6$ cells/µl.

A fifth embodiment of the invention refers to the above defined composition for use in the regeneration of defect of bone or connective tissue, preferably cartilage tissue.

A sixth embodiment of the invention refers to the above defined composition for use in the regeneration of the skin or in the treatment of skin diseases or injuries, preferably acute and chronic ulcers.

A seventh embodiment of the invention refers to the above defined composition for use in the regeneration of periodontal tissue or in the treatment of periodontal diseases, preferably periodontitis.

An eight embodiment of the invention refers to a method for preparing a composition which comprises a substantially pure population of multipotent stromal cells encapsulated in Platelet-Poor Plasma (PPP), wherein the method comprises growing a cell population of multipotent stromal cells in platelet-poor plasma (PPP)

Preferably, the method comprises the following steps:
1. Mixing the stromal cells with PPP;
2. Adding an anti-fibrinolytic agent such as tranexamic acid;
3. Adding a crosslinking agent to start the gelification process;
4. Incubate at 37° C. for 3 to 5 minutes and verify that the mixed has gelified.

More preferably the method comprises:
1. Mixing approximately $1 \times 10^6$ stromal cells in a saline composition with approx. 760 µl of PPP;
2. Adding 15 µl of tranexamic acid;
3. Adding 50 µl of 2% Calcium chloride to start the gelification process;
4. Incubate at 37° C. for 3 to 5 minutes and verify that the mixed has gelified.

The present invention will be further illustrated by the following examples.

EXAMPLES

Material and Methods

Example 1. WST-1 Cell Proliferation Assay

In order to compare the proliferation capacity of UC-MSC (umbilical cord stem cells) between different time points (2, 4, 8 hours, 3 and 7 days) and different temperatures (37° C. and 4° C.), 1.000.000 cells were encapsulated with Plasma Poor in Platelets (PPP) and plated in a 6 well and incubated at 37° C., 5% $CO_2$. At the time of the response, a sample was taken of the original plate using a pouch of 5 mm diameter and transferred to a 96 well plate. The proliferation rate was measured using the WST-1 methods following the manufacturer's instruction (Roche Applied Science, USA). The absorbance was measured using a plate reader (Tecan, USA) at 450 nm with a reference wavelength at 570 nm.

Example 2. Measurement of Growth Factors

The secretion levels of different factors between 3 donors of PPP (0847, 0850 and 0852) and 3 donors of UC-MSC (108-6, 374-5, 745-1) was compared. Vascular endothelial growth factor (VEGF), basic fibroblast growth factor (FGF), and Dental Matrix protein (DMP-1) were measured. In more detail, 500.000 cells were incubated on a 6 well plate in proliferation medium (10% FBS, 1% Penn strep) for 24 hours, the medium was replaced with alpha-MEM containing (2% FBS, 1% penn strep) and the cells were for 24 hours. The supernatants were collected and frozen prior to measurements using the DuoSet ELISA Development System (R&D Systems, Minneapolis) following the manufacturer's instruction.

Example 3. In Vivo Biocompatibilities Assays

All in vivo studies were performed at the animal facility of the Universidad de los Andes (Santiago, Chile) and received approval by the "Universidad de Los Andes ethical committee for animal experimentation". Specifically, different concentration of UC-MSCs were encapsulated with PPP (250.000, 500.000, 1.000.000 and 2.000.000 cells) and injected subcutaneously in 8-week-old NOD.Cg-Prkdcscid Il2rgtm1Wjl/SzJ (NSG) mice (Jackson Laboratories, Bar Harbor, Me.) using a syringe 23G in both flanks of the mouse. After 12 days post-implantation, the mice were euthanized and the implants were removed. The implants were processed for histology and stained with Hematoxylin and Eosin (Sigma). The number of cells was determined using image J software.

Example 4. Isolation and Characterization of DPSC and UC-MSC and In Vitro Expansion Healthy individuals (women and men) aged between 13-26 without any evidence of dental caries was recruited and the third molars were collected in the dental school of Universidad de Los Andes, San Bernardo after signed an informed consent and following the ethical approval of the Universidad de los Andes. Umbilical cords were isolated from full-term human placentas of male newborns collected from caesarean deliveries after informed consent from the maternal donors, and ethical revision and approval from the ethics committees of both the Clinica Davila Hospital and the "Servicio de Salud Metropolitano Oriente" in Chile. The dental pulp stem cells (DPSC) and the umbilical cord stem cells (UC-MSC) were isolated with direct cell outgrowth from the tissue explants. Both explants were incubated for 20 days until the dish reach confluence and MSC with a fibroblast-like morphology were observed. DPSC and UC-MSC were characterized by migration, proliferation potential, immunophenotypic profile, and the capacity to differentiate into adipocytes, chondrocytes and osteoblasts.

Example 5. Immunophenotypical Profile by Flow Cytometry and Mesodermal Differentiation For the immunophenotypic characterization, DPSC or UC-MSC were incubated with the following antibodies: CD105, CD90, CD73, CD34, CD45, CD19 and HLA-DR (BD, USA) for 20 minutes at 4° C. in dark area, then were washed with 4 ml of PBS 1×, centrifuged at 1800 rpm for 6 minutes and the supernatant was removed. Data were collected using a FACS Canto II Flow cytometer (BD Biosciences, San Jose, Calif.) and analysed with FlowJo analysis software. For Adipogenic differentiation, (50.0000 cells) cells were incubated with medium containing ($\alpha$-MEM, 10% FBS, Penn strep (1%), Dexamethasone (0.11 mM), Insulin (10 mg/ml), Indometacin (0.02 mg/ml) for 4 weeks. Then the cells were washed with 1 ml of PBS 1× and stained with 1 m of Oil Red in isopropanol 60% v/v for 1 hour at room temperature. For osteogenic differentiation, (70.000 cells) cells were incubated with medium containing $\alpha$-MEM, 10% FBS, Penn Strep (1%), Dexamethasone (0.1 mM), $\beta$-Glycerophosphate (10 mM) and ascorbate-2 phosphate (50 mg/ml) (Sigma, USA) for 4 weeks. Then the cells were washed with 1 ml of PBS 1× and stained with 1 m of Alizarin Red 40 mM in $NaH_2PO_4$ (0.1M pH 4.3) (Sigma, USA). Finally, for chondrocyte differentiation 60.000 cells were plated in a 10 µl drop in the middle of a 4 well plate for the creation of the micromass. Cells were incubated with medium containing ($\alpha$-MEM, 10% FBS, Penn Strep (1%), Dexamethasone (0.1 mM), Insulin (5 mg/ml), TGF-$\beta$1 (10 ng/ml), Ascorbate-2-phosphate (50 mg/ml) for 4 weeks. Then the cells were washed with 1 ml of PBS 1× and stained with 1 m Safranina O (0.1%) Images were taken with an inverted microscope (Olympus CKX41).

Example 6. AlamarBlue-Cell Proliferation Assay

In order to compare the proliferation capacity between DPSC and UC-MSC, 1000 cells were plated in a 24 well (Nunc, USA) with proliferation medium $\alpha$-MEM (10% FBS and 1% Penn Strep) at 37° C., 5% $CO_2$. The proliferation rate was measured at various time points (day 1, 3, and 9) using the alamarBlue™ (Invitrogen, USA). The fluorescence intensity was measured using a plate reader (Tecan, USA) at 570 nm.

Example 7. In Vitro Scratch Assay

The cell migration was evaluated with a scratch assay. Cells (350.000) were seeded in a 6 well plate with proliferation $\alpha$-MEM (10% FBS and 1% Penn Strep) at 37° C., 5% $CO_2$. After 24 hours of incubation, a scratch was made with a 10 µl pipet tip (Thermoscientific, USA). Images were taken at various time points (0, 4, 8, 12 and 24 hours) using an inverted microscope until the complete closure of the gap. The images were analyzed with the Wimscratch Software (Wimasis, Germany).

Example 8. In Vitro Tube Formation Assay and Measurement of Angiogenic Factors

The angiogenic potential of DPSC or UC-MSC was evaluated based on their capacity to form tube-like structures in vitro (Total Branching Points, Total tube Length, Total Loops). DPSC or UC-MSC (60.000 in total) were seeded on a pre-coated 24 well plate (Nunc, USA) with standard Matrigel matrix (BD Biosciences, USA) and incubated for 5 hours at 37° C., 5% $CO_2$ with EGM medium (Lonza, USA). Additionally, to determine the angiogenic potential of MSC conditioned media (CM), 500.000 cells (DPSC or UC-MSC) were incubated under hypoxic (1% $O_2$) or normoxic conditions for 48 hours. Subsequently, HUVEC (human umbilical vein endothelial cells) were plated with the MSC-CM, EGM-2 (endothelial growth medium) as positive control or $\alpha$-MEM (negative control) coated with Matrigel Matrix. In both in vitro experiments described previously, images were taken after 5 hours of incubation with an inverted microscope and analyzed with the Wim-Tube software (Wimasis, Germany). Finally, the different MSC-CM was collected and the secreted levels of VEGF and HGF were measured using the DuoSet ELISA Development System (R&D Systems, USA) following the manufacturer's instruction.

Example 9. Matrigel Plug Assay

To compare the angiogenic potential of DPSC and UC-MSC in vivo, the Matrigel plug assay was performed in an 8-week-old NOD.Cg-Prkdc$^{scid}$ Il2rg$^{tm1wjl}$/SzJ (NSG) mice (Jackson Laboratories, Bar Harbor, Me.). All in vivo studies received approval by the Universidad de Los Andes ethical committee for animal experimentation. Additionally the authors have completed and complied with the Animal Research: Reporting of In Vivo Experiments guidelines/checklist for preclinical animal studies. Specifically 3.000.000 cells were mixed with 250 µl of Matrigel HC GFR (BD, USA) with 50 ng/ml VEGF (R&D Systems, USA) and injected subcutaneously using a syringe 23G in both flanks of the mouse (2 Matrigel plugs per mouse-6.000.000 cells). The mice (24 mice in total) were divided into 4 different groups: 1) Matrigel alone 2) UC-MSC+Matrigel, 3) DPSC+Matrigel and 4) HUVECS+Matrigel (positive control). After 14 days post-implantation, the mice were euthanized and the plugs were removed. Images were taken of the implanted plugs and the quantity of new vessels formed around the implants was quantified with image J. The matrigel implants were homogenized and Hemoglobin content of the implant was determined by Drabkins reagent kit (Sigma, USA).

Example 10. Platelets Poor Plasma (PPP) Scaffold Fabrication and In Vitro Biocompatibility of DPSC and UC-MSC PPP (500 ml) was purchased from Clinica Universidad de los Andes, Chile. To avoid several freeze-thaw cycles, PPP was aliquoted it in falcon tubes (50 ml) and maintained at −80° C. until further used. To prepare a PPP scaffold (5 ml of PPP total), 1×10$^6$ cells were mixed with 3800 µl of PPP, 875 µl $\alpha$-MEM (10% FBS and 1% Penn Strep), 75 µl of tranexamic acid and 250 µl of 2% Calcium chloride and transferred in a 6 well plate (Nunc, USA) and placed at 37° C. until further use. The in vitro biocompatibility was evaluated with alamarBlue (Invitrogen, USA) after 1, 3, 7 and 14 days. The time of the response several punches with a 5 mm diameter punch was generated (Dolphin Medical, Chile) in the PPP. Each punch was placed in a 96 well plate with 200 µl of culture medium and 20 µl of alamarBlue reagent and incubated for 2 hours at 37° C. After the incubation period 100 µl of the supernatant were transferred in a fresh 96 well plate and the absorbance was measured according to the manufacturer instructions. In parallel, punches of PPP scaffolds for each time point (1, 3, 7 and 14 days) were fixed in 10% formalin solution and processed for histological analysis. The scaffolds were stained for hematoxylin and eosin (Sigma, USA).

Example 11. Ultra-Structural Analysis of PPP Scaffolds

In order to evaluate the ultra-structural analysis, at different time points, Scanning Electron Microscopy (SEM) was used to investigate the structure, morphology of the PPP scaffolds with or without cells. The 5 mm punches of PPP scaffolds described previously were fixed with 2.5% gluteraldehyde (Sigma, USA), dehydrated in a progressive series of ethanol before being mounted on an aluminum stub using silver paint. Samples were coated with gold/palladium before examination under a JSM-7500F scanning electron microscope (JEOL, USA).

Example 12. Measurement of Released Protein Factors from PPP

An ELISA was performed in order to evaluate the release protein profile of PPP with or without encapsulated cells (DPSC/UC-MSC). PPP scaffolds were manufactured as described previously. After 24 hours incubation, the supernatant (Culture Medium-CM) was collected and the PPP was carefully detached, lifted from the 6 well plate and finally squeezed using a 10 ml syringe (BD, USA) with a 16G needle (Hamilton, USA) until all the exudate of the PPP was completely removed. The two different liquids (Supernatant+Exudate) were processed and the secreted levels of VEGF, HGF and DMP-1 were measured using the DuoSet ELISA Development System (R&D Systems, USA) following the manufacturer's instruction (8).

Example 13. Preparation of Dentin-Discs/PPP Scaffolds and Implantation into a Mouse Subcutaneously Human molar teeth extracted from healthy individuals as described previously were sliced horizontally with thickness of 3 mm and length 0.5 mm using a Dremel (Sodimac, Chile) (The volume of the root canal space was 40 µl). To ensure no microbial contamination, the dentin-discs were sterilized 17% ethylenediaminetetraacetic acid for 10 minutes and 19% citric acid for 1 min to remove the smear layer, followed by treatment with betadine for 30 minutes and 5.25% NaOCl for 10-15 minutes Finally, discs were rinsed in sterile PBS and incubated at 37° C. for 3-7 days. Cells ($1\times10^6$) were mixed with 760 µl of PPP, 175 µl α-MEM (10% FBS and 1% Penn Strep), 15 µl of tranexamic acid and 50 µl µl of 2% Calcium chloride in a 1.5 centrifuge tube. Upon coagulation, PPP was detached and lifted carefully using a pair of tweezers and placed into the canal space of each root a fragment and kept in a 6 well plate with proliferation medium (α-MEM) at 37° C. until further use. The constructs were placed subcutaneously in mice 6-8 weeks old NOD.Cg-Prkdcscid Il2rgtm1Wjl/SzJ (NSG) mice (Jackson Laboratories, Bar Harbor, Me.). The mice were anesthetized using zivofluoran 15 mg/kg and the implants were place in a subcutaneous pocket. Each mouse received two Dentin-Discs/PPP Scaffolds and incubated for 4 weeks. The mice were euthanized using $CO_2$ and images were taken of the implant discs while still positioned on the mouse skin in order to quantify new vessels formed around Dentin-Discs/PPP Scaffolds using image J as described previously. Thereafter, the implants were removed and placed in 10% formalin (Sigma, USA) and then decalcified for 2 months using formic acid (Sigma, USA) Finally, were paraffin embedded and longitudinally sectioned 4 µm and stained for hematoxylin and Eosin (Sigma, USA). Some of the sections were used for immunohistochemical analysis. All animal procedures followed a protocol approved by the Institutional Animal Care and Use Committee at the Universidad de los Andes.

Example 14. Immunohistochemistry

For Immunohistochemistry, Deparaffinized sections were dehydrated in a series of xylol and alcohol series and then the antigen recuperation was performed using citric buffer. The samples were immersed in 3% $H_2O_2$ for 15 minutes and then blocked with BSA for 30 minutes. After the primary incubation overnight at 4° C. was performed using the following antibodies: 1) Human leukocyte antigen (HLA), Dentin Sialoprotein (DSPP) (all purchased from ABCAM). Isotype-matched control antibodies were used under the same conditions as the primary antibodies. For enzymatic immunohistochemical staining, VECTASTAIN® Universal ABC kit (Vector Laboratories, USA) according to the manufacturer's protocol. All sections were contain stain with hematoxylin and mounted with a 10 µl drop of Entellan (MercK). The amount of protein expression was calculated with image J and was expressed as % area.

Example 15. Statistical Analysis

All the experiments were performed in biological and experimental triplicated and the values expressed as mean. The comparisons between the groups were made with ANOVA post-hoc Tukey test. A probability value of P<0.05 (*), P≤0.01 (), P≤0.001 (*) and P≤0.0001 (****) was considered statistically significant.

Results.

Example 16. Proliferation Capacity of PPP Encapsulated MSCs

UC-MSCs and DPSCs (dental pulp stem cells) extracted from the tissue were cultured with DMEM (10% FBS and 1% Pen strep) until reaching passage 3-4. Similarly to previous observations, MSCs from both sources showed similar fibroblast-like characteristics as other mesenchymal stem cells used in our laboratory. DPSCs showed higher proliferation rate as counted in H&E staining of PPP (FIG. 1A) as day 7 and 14 post-culture. Electonic microscopy showed a change in the PPP structure post-culture independently of the source of MSCs used. An increased porosity was detected starting at day 7 in PPP with MSCs in comparison to the condition where cells were not added (FIG. 1B). Additionally, the proliferation of UC-MSCs between different time points and incubation temperatures was investigated using a WST-1 cell proliferation assay. No significant difference was observed in the proliferation of UC-MSCs between 2-24 hours at both temperatures (37° C. and 4° C.). A significant increase in the proliferation of UC-MSCs at day 3 and day 7 (p<0.05) was observed of UC-MSCs incubated at 37° C. compared to 4° C. (FIG. 2A). This is relevant to assess the shelf-life and transport conditions under which the therapeutical product biological activity remains unchanged.

Example 17. Measurement of Protein Content of PPP and UC-MSCs

Although the mechanism of action (MOA) of MSCs is not completely clear, it has been suggested that their therapeutic activity may be mediated by a paracrine effect. The aim of the secretome study was to evaluate the amount of secreted factors relevant to the tissue regeneration. VEGF is a signal protein secreted by cells that stimulates vasculogenesis and angiogenesis. FGF is a growth factor involved in angiogenesis, wound healing and various endocrine pathways. DMP-1 (dentin matrix acidic phosphoprotein) is an extracellular matrix protein critical for proper mineralization of bone and dentin, and is present in diverse bone and tooth tissues.

The amount of protein released was measured with an ELISA for VEGF, FGF and DMP-1. 3 different donor of UC-MSCs were seeded in 6 well plates and cultured for 24 hours with 2% FBS (see FIG. 1)

Figure 2:
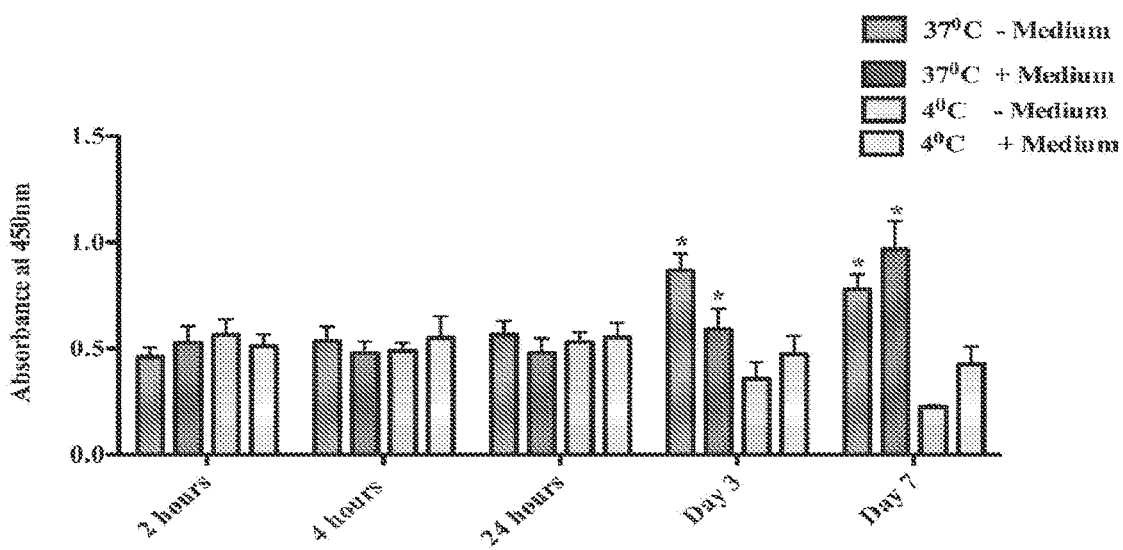
FIG. 2. (A) Quantification of cell proliferation between UC-MSC incubated at different time points. At day 3 and 7, an increase in the proliferation of UC-MSC at 37° C. compared 4° C. was observed (p<0.05). (B, C and D) In vitro release of different proteins (VEGF, FGF and DMP-1) between 3 different donors of PPP and UC-MSC. The results have shown a higher protein release for the donor UC-MSC (374-5) and donor 0850 for PPP with a, p<0.05. (E, F and G) Proliferation rate of encapsulated UC-MSC in PPP in vivo. (E) Histological staining of UC-MSC encapsulated in PPP at day 1 (pre-implantation) and (F) at day 12 (post implantation). (G) Cell counting based on image J analysis has shown that a significant number of cells after 12 days of implantation compared to day 1. All data are represented as a mean with the associated SEM (n=3) of a minimal four donors.
Figure 2:
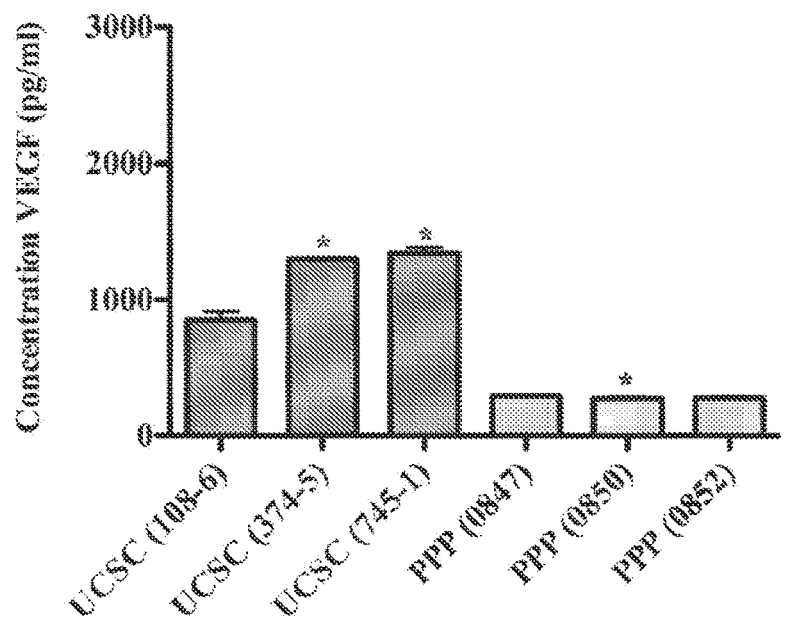
Figure 2:
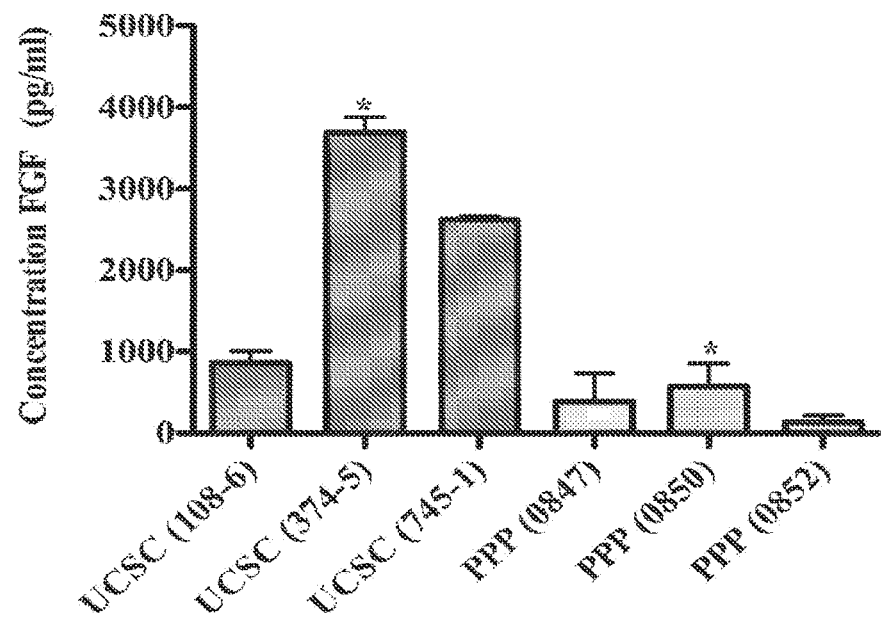
Figure 2:
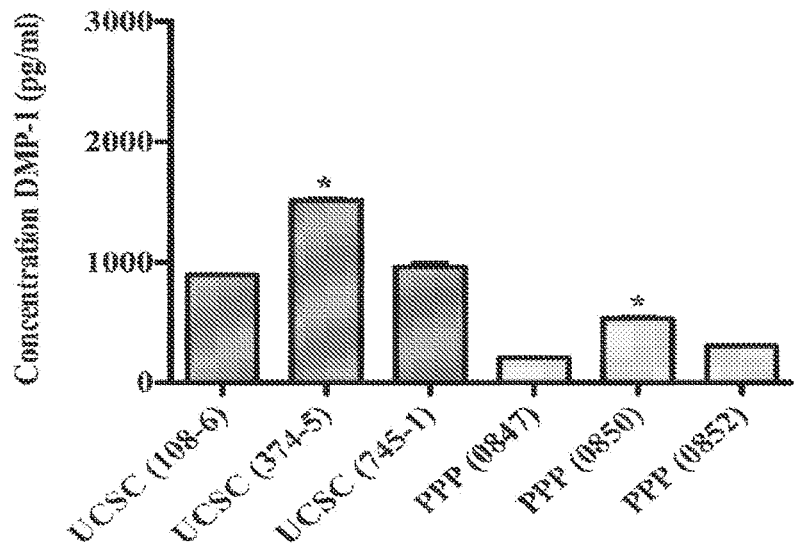
Figure 2:
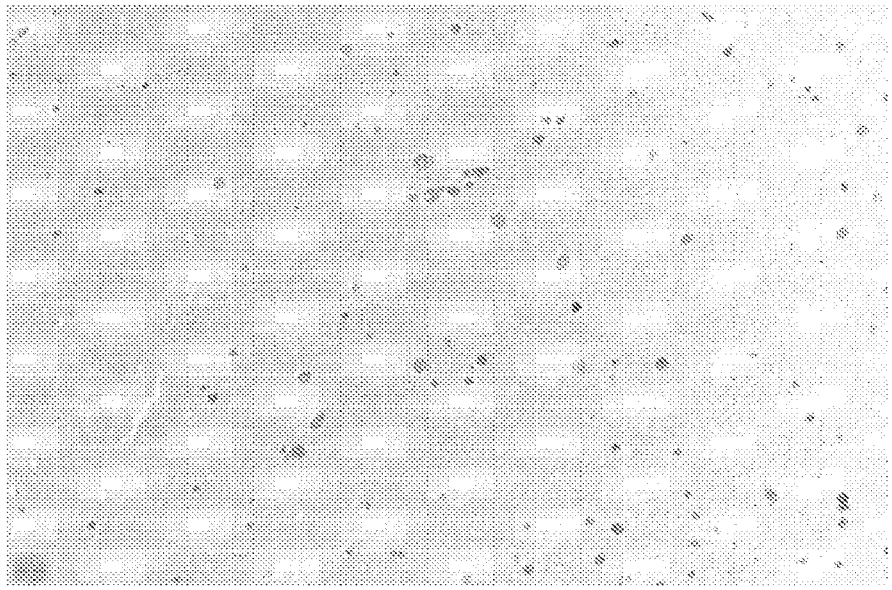
Figure 2:
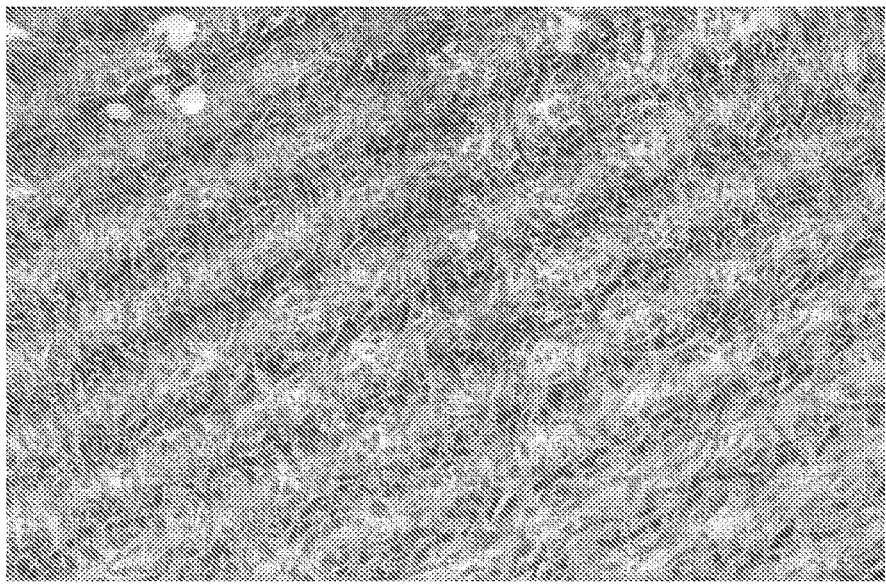
Figure 2:
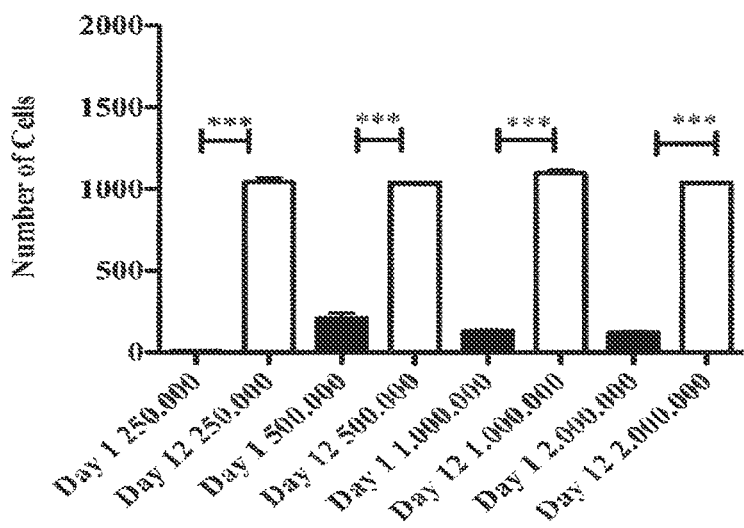

Example 18. Proliferation Capacity of UC-MSCs Encapsulated or Grown in PPP after 12 Days In Vivo In order to evaluate the proliferation capacity of different doses of encapsulated cells in PPP, we have tested different concentrations of UC-MSCs (250.000, 500.000, 1.000.000 and 2.000.000). The UC-MSCs were injected in vivo for 12 days. After 12 days, the implants were removed and processed for histology. The number of cells were counted using image J. The results show a significant increase in the number of cells after 12 days of implantation compared to day 1 (pre-implantation) as shown in FIGS. 2 (E),(F) and (G).

Example 19. DPSC and UC-MSC Display a High Proliferation Rate

Both cell sources showed a positive expression of the common MSC markers such as CD105, CD90, CD73, CD34, CD45, CD19 and HLA-DR (FIG. 9A) and also DPSC and UC-MSC were induced to differentiate into mesodermal tissues (adipopogenic, chondrogenic and osteogenic) lineages (FIG. 9B). No apparent differences were observed between DPSC or UC-MSC and also their multipotency (osteogenic, chondrogenic, adipogenic).

Figure 3:
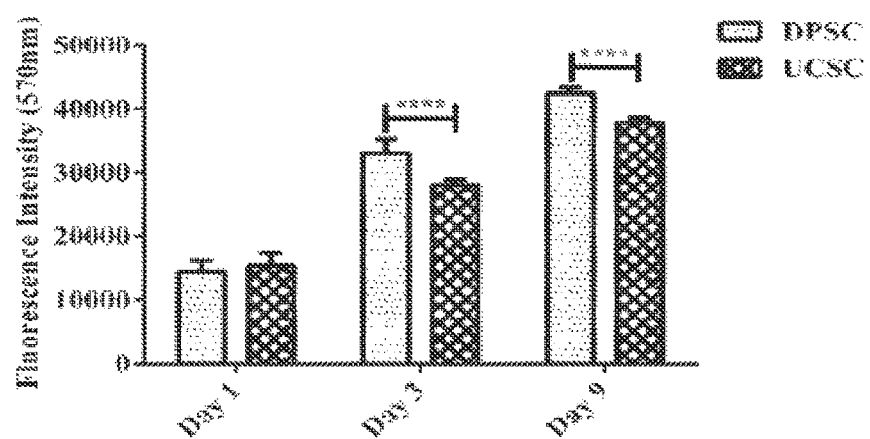
FIG. 3. (A). The proliferation between DPSC and UC-MSC was investigated using an Alamar Blue cell proliferation assay. A significant increase in the proliferation of DPSC at day 3 and day 9 with 1.2 and 1.1 fold increases respectively was observed (P<0.0001). (B+C) indicates that UC-MSC possess a higher migration potential in comparison to DPSC for the different time points analyzed.
Figure 3:
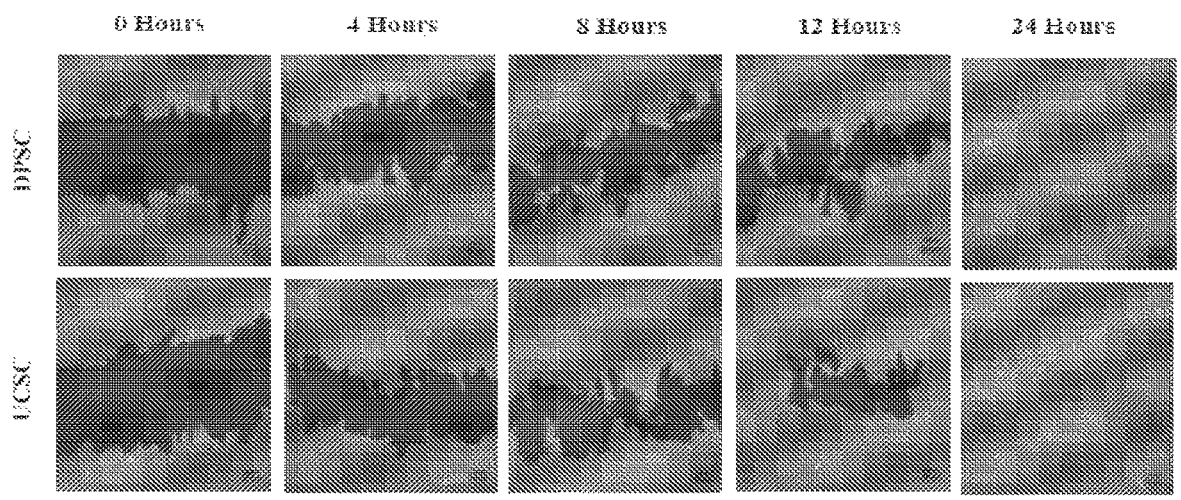
Figure 3:
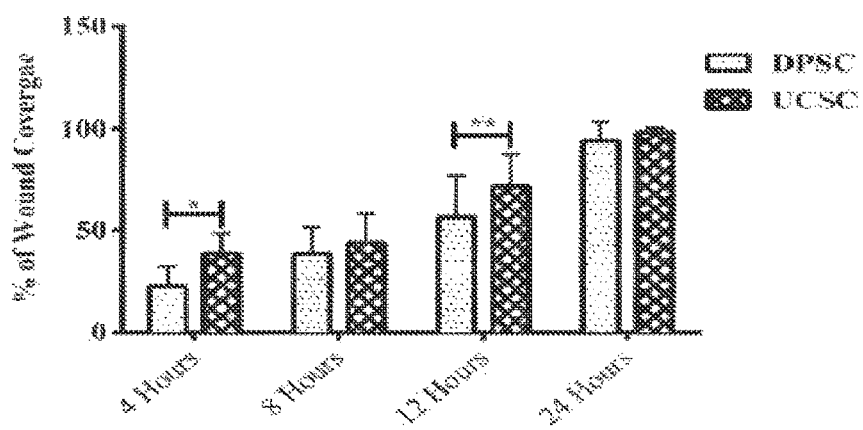

DPSC and UC-MSC have shown previously similar fibroblast-like characteristics. Additionally, the proliferation between the DPSC and UC-MSC was investigated using an Alamar Blue cell proliferation assay. A significant increase in the proliferation of DPSC at day 3 and day 9 with 1.2 and 1.1 fold increase respectively ($P<0.0001$) (FIG. 3 A).

Example 20. UC-MSC Exhibit a Superior Migratory Capacity in a Wound Scratch Assay To evaluate the migration potential of DPSC and UC-MSC, a wound scratch assay was performed. The migratory capacity was evaluated from each time point (0, 4, 8 and 12 hours) in correlation to 0 hours. There was a significant increase in the migration of UC-MSC compared to DPSC for 4 and 12 hours with 1.2 ($P<0.05$) and 1.4 fold ($P\leq0.01$) increase respectively. No significant difference was observed at 8 hours and at 24 hours where in the latter time point full wound closure was reached by both cell sources. This experiment indicates that UC-MSC possess a higher migration potential in comparison to DPSC for the different time points analysed (FIG. 3 B+C).

Figure 4:
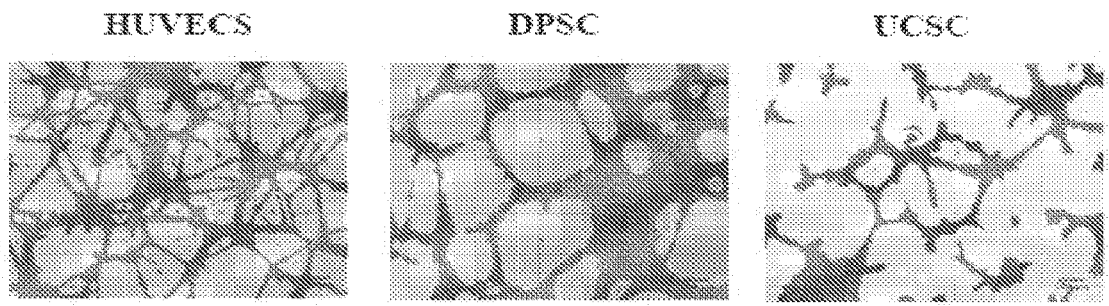
FIG. 4. (A, B, C, D) Image analysis of the tube formation evaluated at 5 hours post-culture initiation showed a higher angiogenic capacity evidenced by a more extensive network of capillary-like structures for DPSC as compared to UC-MSC. (E) Images were taken and the results have shown a higher tubular structure for the HUVECS incubated with the conditioned medium under hypoxic conditions vs normoxic. (F, G, H) There was a significant difference between the formation of total tube lengths, total loops and total branching points between hypoxia DPSC and hypoxia UC-MSC. (I, J) The quantification of angiogenic factors revealed a non-significant difference in the VEGF release for DPSC compared to UC-MSC after 8 hours of incubation under hypoxic conditions.
Figure 4:
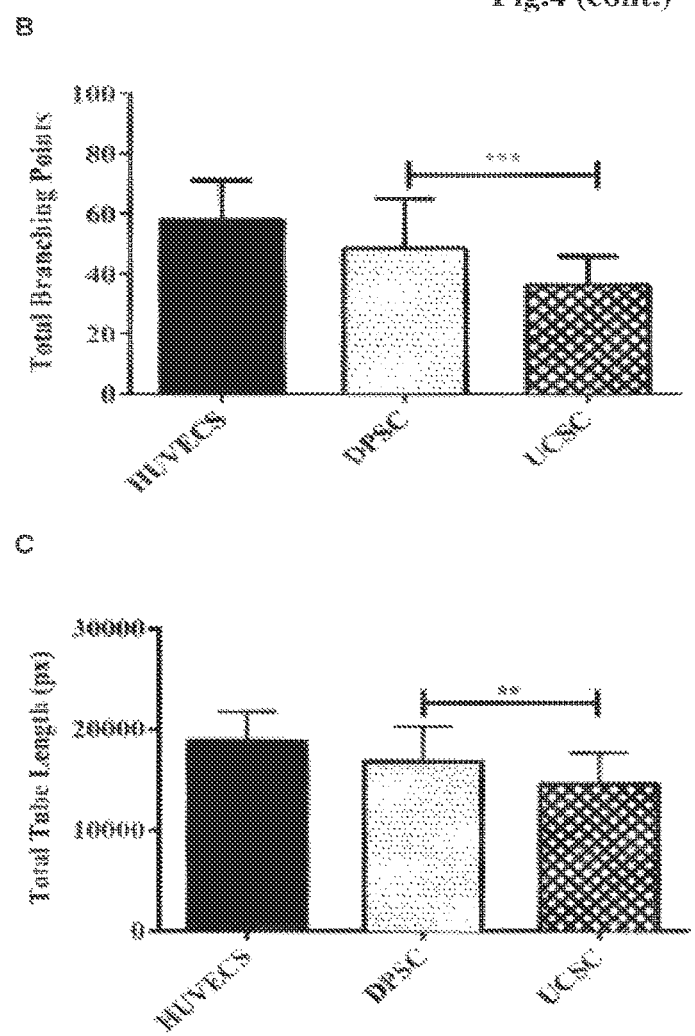
Figure 4:
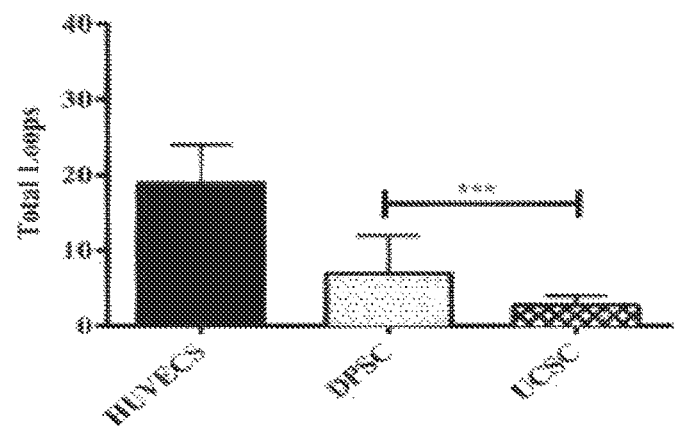
Figure 4:
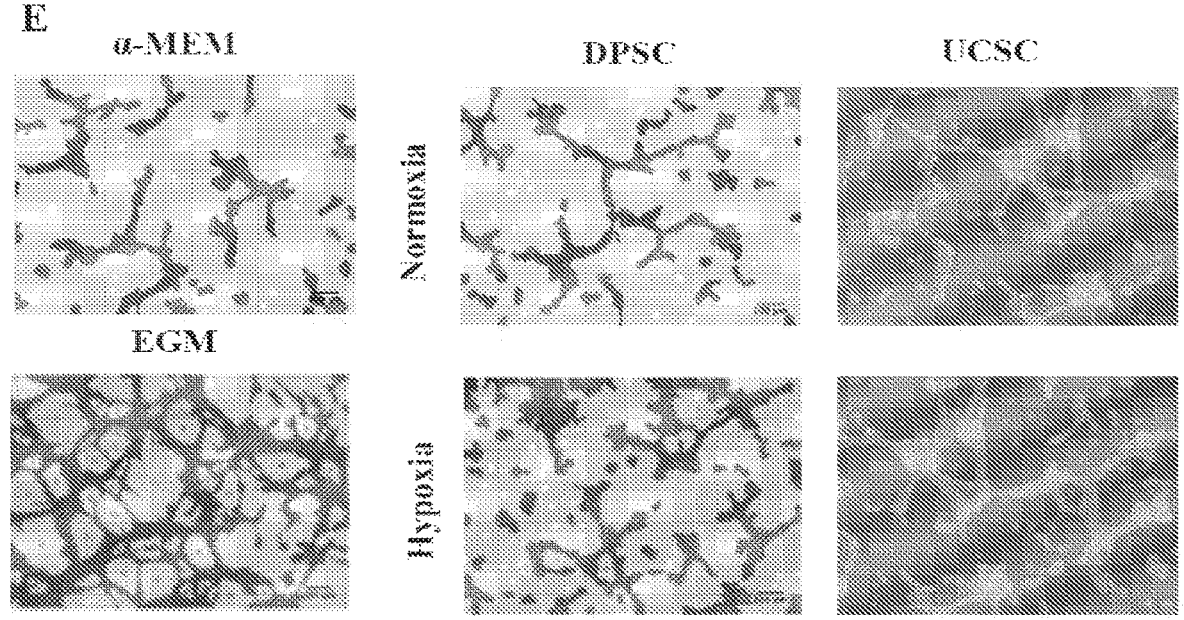
Figure 4:
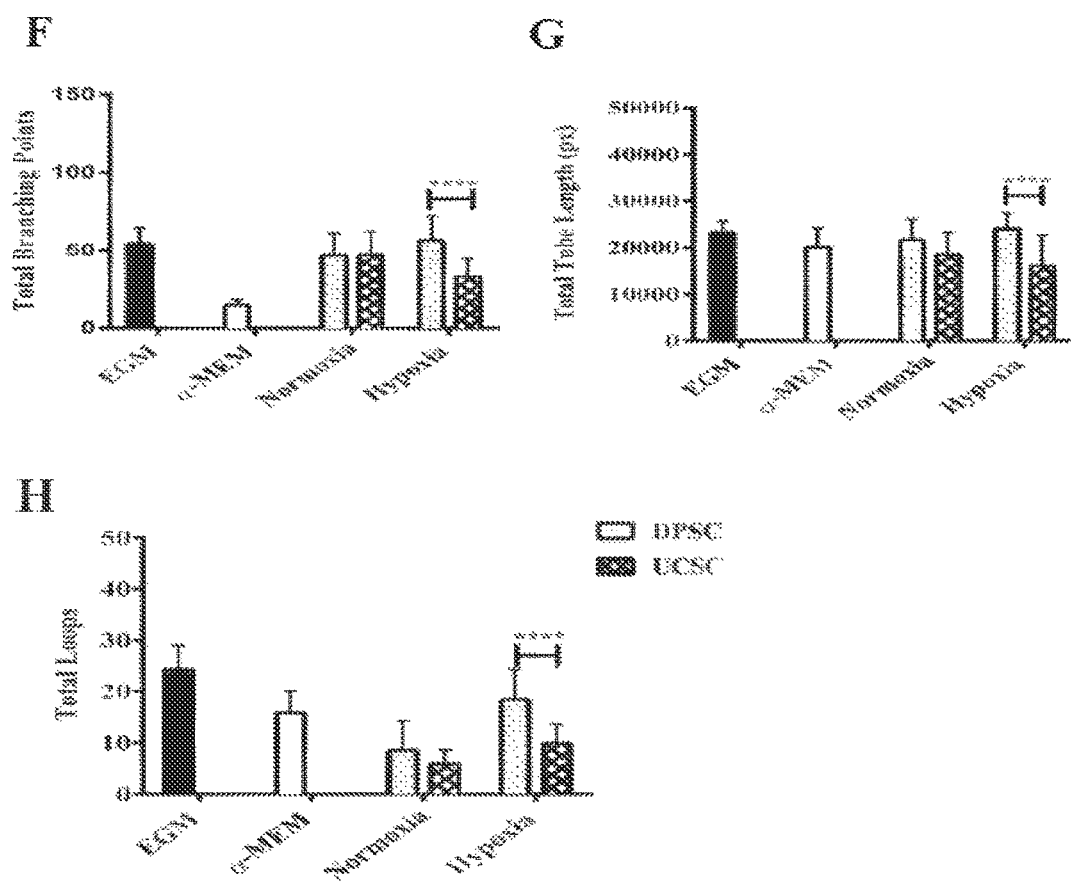
Figure 4:
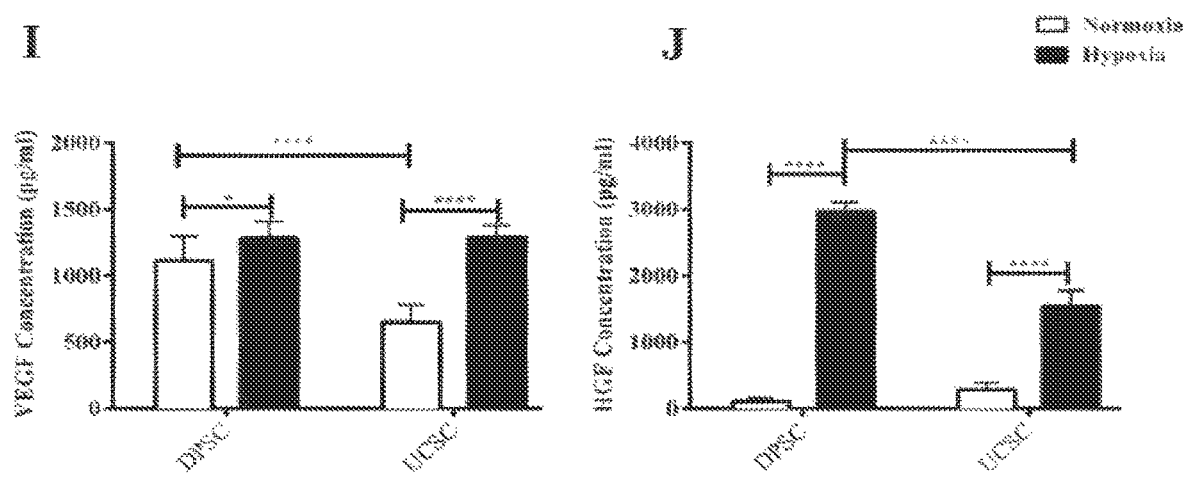

Example 21. DPSC and UC-MSC were Able to Form a High Number of Tube-Like Structures The angiogenic ability designated by the ability of DPSC and UC-MSC to form tubular network was investigated in vitro in a semi-solid medium (Matrigel). The in vitro angiogenesis was evaluated with following characteristics: 1) total branching points, 2) total tube length and 3) total loops (FIG. 4 A). Image analysis of the tube formation evaluated at 5 hours post-culture initiation, showed a high angiogenic capacity evidenced by an extensive network of capillary-like structures for DPSC and UC-MSC. Specifically a 1.3 total branching points increase ($P\leq0.001$), 1.15 fold change total tube length ($P\leq0.01$) and a 2.5 fold change for total loops ($P\leq0.001$) (FIG. 4 B+C+D). In order to evaluate their secreted paracrine factors, we assessed the angiogenic potential of released factors from the conditioned media (CM) harvested from DPSC and UC-MSC after 48 hours incubation under hypoxic (1% O2) or normoxic conditions. HUVECS were re-suspended with the CM and were seeded onto pre-coated plated with growth Factor Reduced Matrigel. Alpha-MEM (basal media) and EGM (angiogenic media) were used as the negative and positive controls, respectively. The tube formation was analyzed after 5 hours of incubation Images were taken and the results have shown a higher tubular structure for the HUVECS incubated with the conditioned medium under hypoxic conditions vs normoxic (FIG. 4 E). There was a significant difference between the formation of total tube lengths, total loops and total branching points between hypoxia DPSC and hypoxia UC-MSC. Specifically, a 1.7 fold change for total branching point increase ($P\leq0.0001$) 1.4 fold change for total tube length ($P\leq0.0001$) and a 1.8 fold change for total loops ($P\leq0.0001$) as showed in FIG. 4 F+G+H. The quantification of angiogenic factors (FIG. 4 I+J) revealed a non-significant difference in the VEGF release for DPSC compared to UC-MSC after 8 hours of incubation under hypoxic conditions. The release of HGF was 1.9 fold change ($P\leq0.0001$) higher after 48 hours of incubation for both DPSC compared to UC-MSC after incubation under hypoxic conditions.

Example 22. Angiogenic Potential of UC-MSC and DPSC In Vivo

Figure 5:
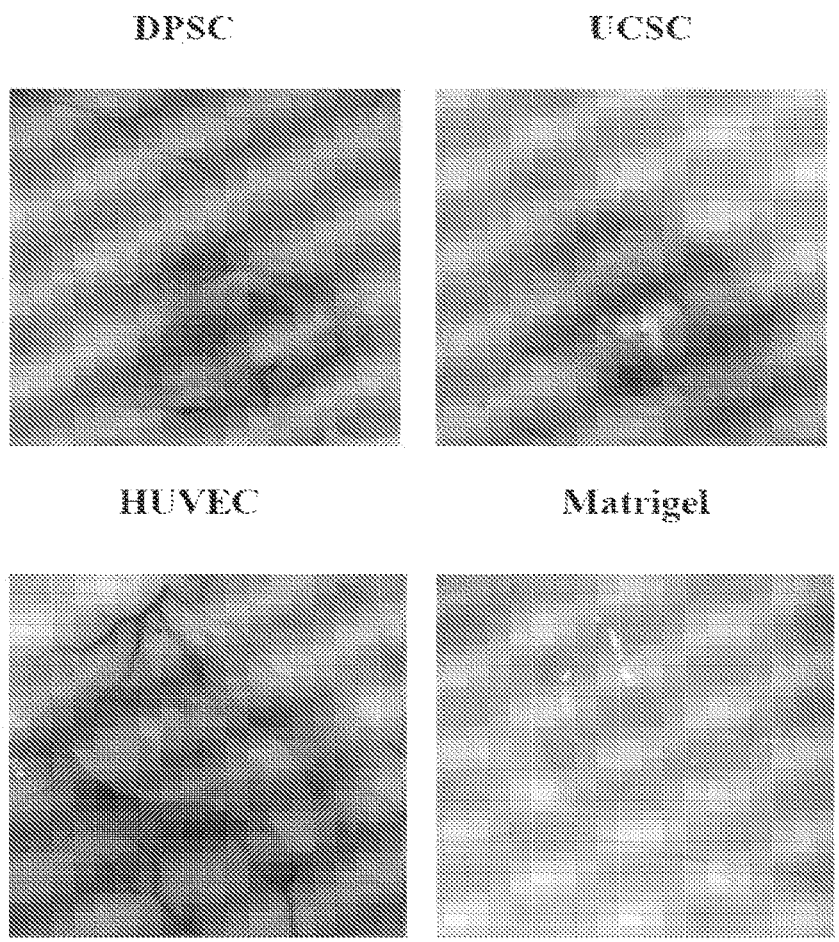
FIG. 5. (A) All plugs generated vessels around and inside the implant. (B) The image analysis of the implants showed a non-significant difference in the vessel formation between DPSC and UC-MSC. (C) The results have shown a 6.2 fold change higher hemoglobin content of DPSC compared to Matrigel (negative control) (P≤0.0001) and 5.1 fold change difference between UC-MSC and Matrigel (negative control).
Figure 5:
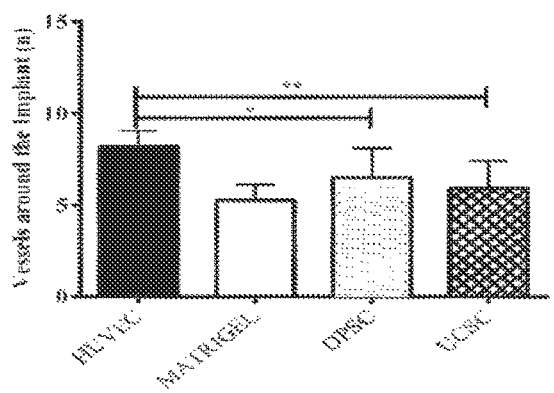
Figure 5:
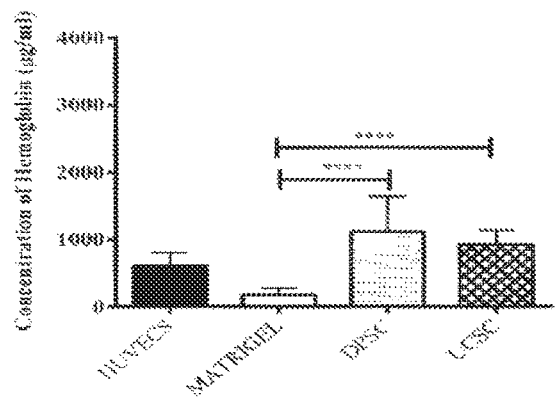

To comparatively evaluate the angiogenic potential of DPSC and UC-MSC a Matrigel plug was implanted in NSG mice. After 15 days the implants were collected and photographs were taken. As shown in FIG. 5 all plugs generated vessels around and inside the implant. The image analysis pf the implants showed a non-significant difference in the vessel formation between DPSC and UC-MSC (FIG. 5 B). Additionally, the implants were extracted and analyzed for their hemoglobin content. The results have shown a 6.2 fold change higher hemoglobin content of DPSC compared to Matrigel (negative control) ($P\leq0.0001$) and 5.1 fold change difference between UC-MSC and Matrigel (negative control) (FIG. 5 C).

Figure 6:
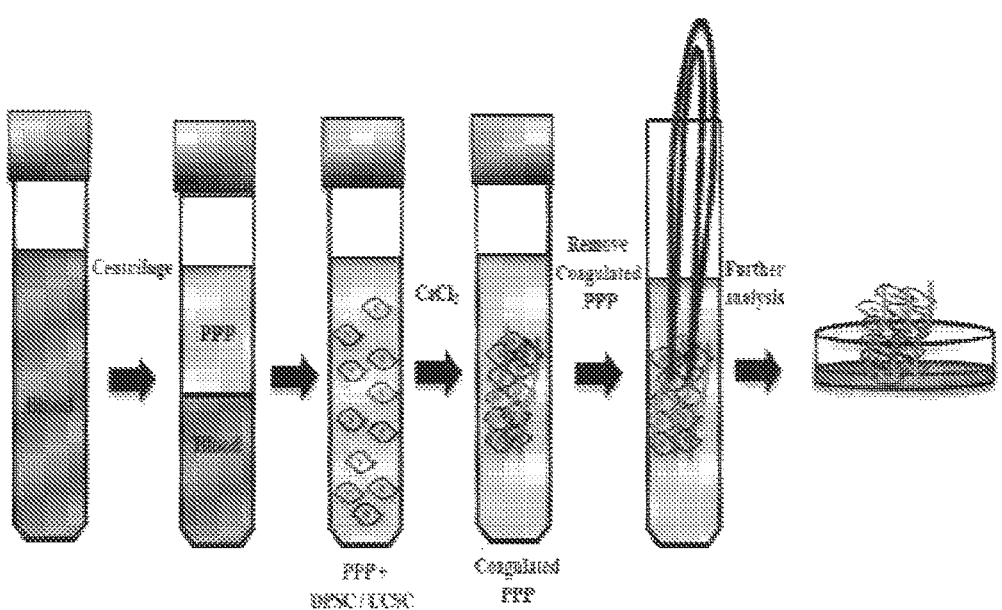
FIG. 6. (A) UC-MSC or DPSC were encapsulated in PPP scaffolds and cultured for various time points in vitro. (B) The results have shown that DPSC and UC-MSC were attached and proliferated on the PPP scaffold at various time points. The proliferation of DPSC or UC-MSC encapsulated in PPP was evaluated with alamarBlue. The results have shown an 1.5 (P<0.05), 3.1 (P≤0.0001) and 3 fold change (P≤0.0001) respectively increase in the proliferation between DPSC+PPP vs PPP alone at day 3, day 7 and day 14. Also 1.8 fold change (P≤0.0001) and 2.8 fold change (P≤0.0001) increase was observed between UC-MSC+PPP vs PPP alone at day 7 and 14. Finally, a significant different 1 fold (P≤0.0001) was observed between UC-MSC+PPP and DPSC+PPP at day. (C) Histological sections of UC-MSC or DPSC have revealed an increase in the cell number for DPSC and UC-MSC which coincide with the proliferation results. (D) SEM images revealed a porous structure of the PPP with random fibrin fiber spread around the biomaterial surface. PPP encapsulated with either DPSC or UC-MSC has shown an apparent increase in the porosity after 14 days of incubation.
Figure 6:
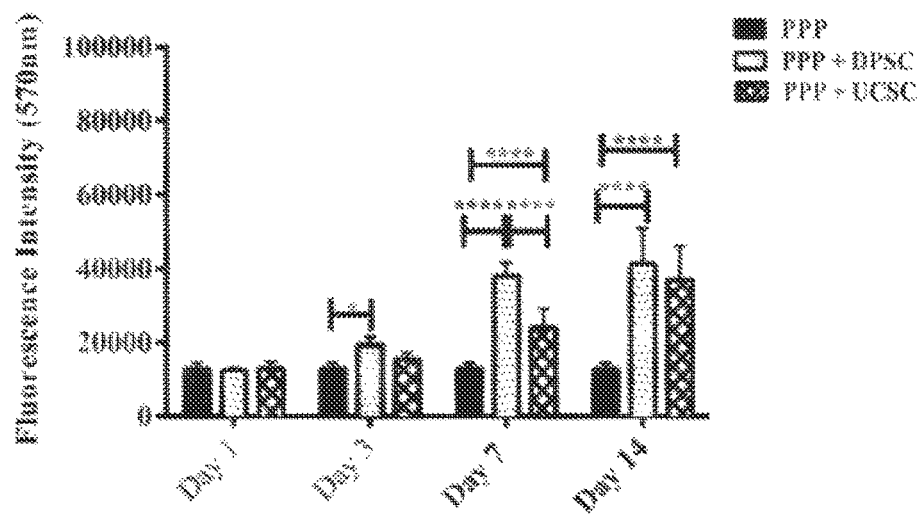
Figure 6:
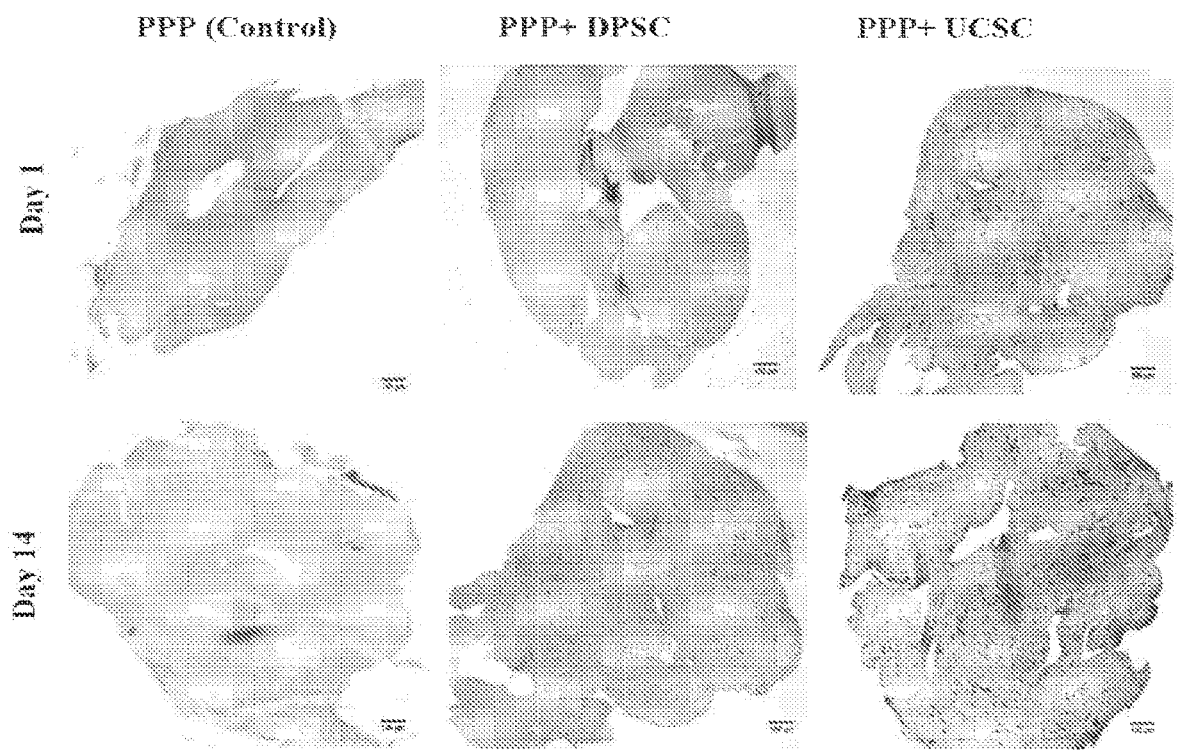
Figure 6:
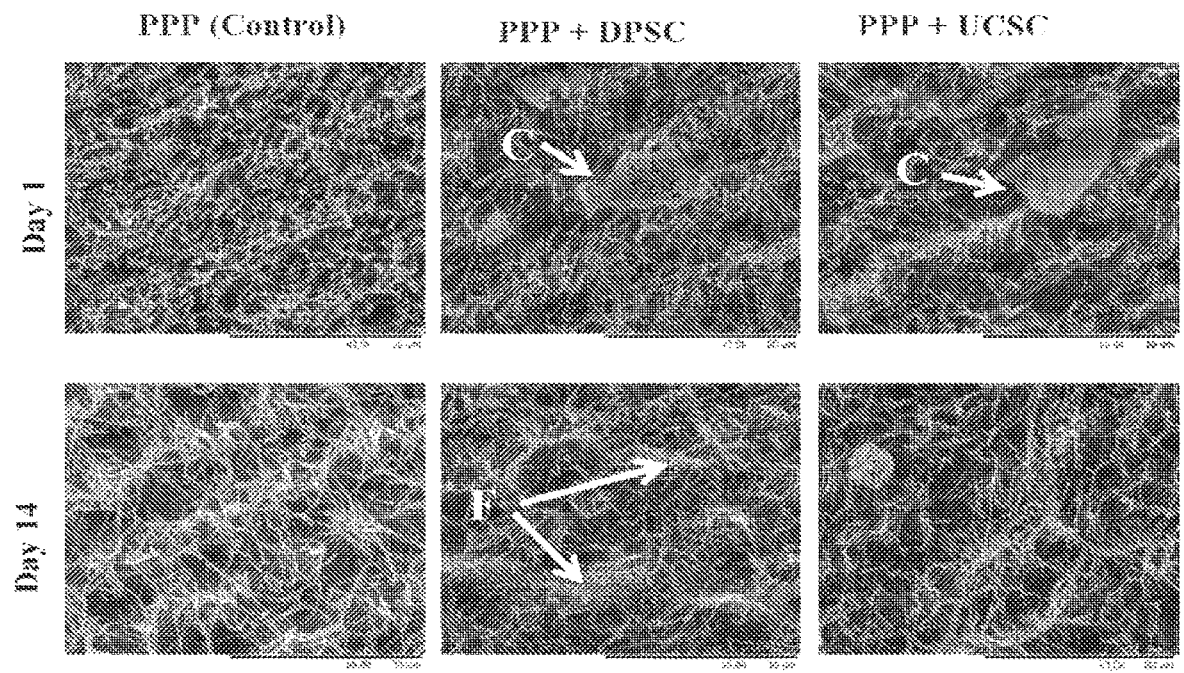

Example 23. Cytocompatibility of DPSC or UC-MSC Encapsulated on PPP Scaffolds and Ultrastactural Analysis UC-MSC or DPSC were encapsulated in PPP scaffolds and cultured for various time points in vitro (FIG. 6A). The results have shown that DPSC and UC-MSC were attached and proliferated on the PPP scaffold at various time points. The proliferation of DPSC or UC-MSC encapsulated in PPP was evaluated with alamarBlue. The results have shown a 1.5 ($P<0.05$), 3.1 ($P\leq0.0001$) and 3 fold change ($P\leq0.0001$) respectively increase in the proliferation between DPSC+PPP vs PPP alone at day 3, day 7 and day 14. Also 1.8 fold change ($P\leq0.0001$) and 2.8 fold change ($P\leq0.0001$) increase was observed between UC-MSC+PPP vs PPP alone at day 7 and 14. Finally, a significant different 1 fold ($P\leq0.0001$) was observed between UC-MSC+PPP and DPSC+PPP at day 14 (FIG. 6B).

Histological sections (FIG. 6C) of UC-MSC or DPSC have revealed an increase in the cell number for DPSC and UC-MSC which coincide with the proliferation results. SEM images (FIG. 6D) revealed a porous structure of the PPP with random fibrin fiber spread around the biomaterial surface. PPP encapsulated with either DPSC or UC-MSC has shown an apparent increase in the porosity after 14 days of incubation.

Figure 7:
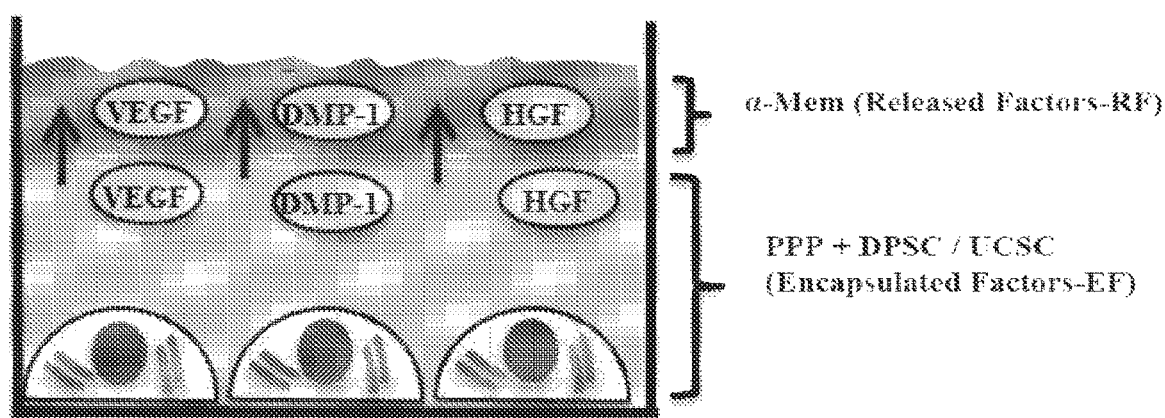
FIG. 7. (A) An ELISA of different protein factors was used such as VEGF, FGF, and DMP-1 in order to investigate the release profile of PPP with or without cells. (B) There was a 1.3 fold increase (P≤0.01) in the protein expression of the encapsulated VEGF (EF) between PPP+DPSC and PPP+UC-MSC after 24 hours of incubation. (C) Also, a 2.1 fold increase of (P≤0.0001) increase in the protein expression of the encapsulated FGF (EF) after 24 hours between PPP+DPSC and PPP+UC-MSC. (D) Finally, for protein DMP-1 protein expression, there was a 1.1 fold change change (P<0.05) between released (RF) PPP and released PPP+DPSC after 24 hours of incubation. No significant difference was observed in the protein expression between PPP+DPSC and PPP+UC-MSC encapsulated factors (EF) or released factors (RF) after 24 hours of incubation. These results have suggested that DPSC encapsulated in PPP produce more protein factors compared to encapsulate UC-MSC in PPP.
Figure 7:
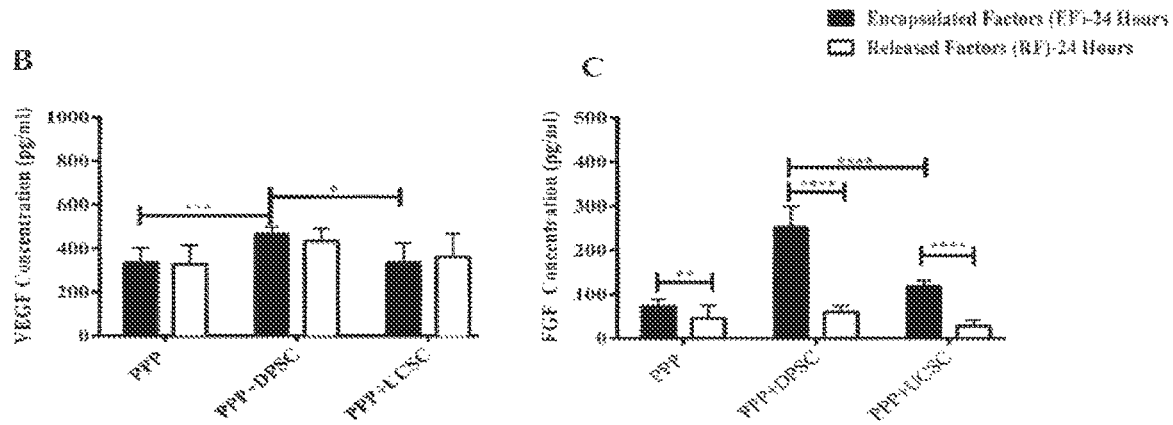

Example 24. Quantification of the Release Protein Profile of PPP after DPSC/UC-MSC Encapsulation In order to investigate the release profile of PPP with or without cells an ELISA of different protein factors were used such as VEGF, FGF, and DMP-1 as shown in FIG. 7A. The results have shown that there was a 1.3 fold increase ($P\leq0.01$) in the protein expression of the encapsulated VEGF (EF) between PPP+DPSC and PPP+UC-MSC after 24 hours of incubation (FIG. 7B). Also, a 2.1 fold increase of ($P\leq0.0001$) increases in the protein expression of the encapsulated FGF (EF) after 24 hours between PPP+DPSC and PPP+UC-MSC (FIG. 7C). Finally, for protein DMP-1 protein expression, there was a 1.1 fold change change ($P<0.05$) between released (RF) PPP and released PPP+DPSC after 24 hours of incubation. No significant difference was observed in the protein expression between PPP+DPSC and PPP+UC-MSC encapsulated factors (EF) or released factors (RF) after 24 hours of incubation. These results have suggested that DPSC encapsulated in PPP produce more protein factors compared to encapsulated UC-MSC in PPP (FIG. 7D).

Figure 8:
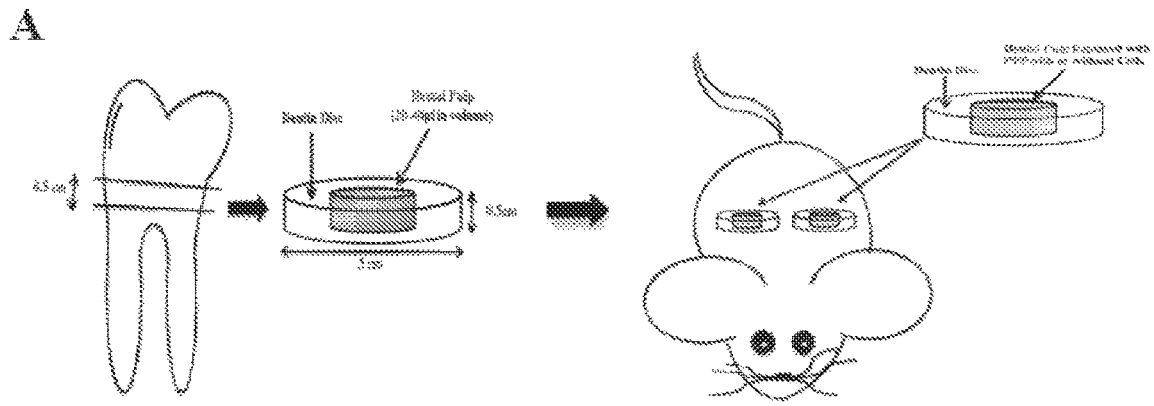
FIG. 8. (A) The dentin-discs/PPP scaffolds were implanted subcutaneously for 30 days. (B) Images were taken of the implants prior removal and an evaluation of the vessel formation around the dentin dentin-discs/PPP was performed. (C) The results have shown a 1.6 fold increase (P≤0.01) in vessels formation around the dentin-disc for the PPP+DPSC compared to PPP alone. (D) The hematoxylin and eosin results have shown that DPSC or UC-MSC were well incorporated in the PPP and migrated towards the dentin wall forming a dense layer of new mineralized dentin-like tissue. (E) Immunohistochemical staining revealed a positive staining for dentin sialoprotien (DSPP) which implies the formation of new dentin and odontoblast formation for either DPSC or UC-MSC. (F) The results have shown a 28.1 fold change (P≤0.0001) increase for PPP+DPSC compared to PPP alone and 28.5 fold change (P≤0.0001) difference for PPP+UC-MSC compared to PPP. (G) The majority of the cells stained positively for the antibody confirming the human cell origin of these cells. (H) Histological analysis of Dentin-Disc/PPP model after 30 days of implantation subcutaneously in a mouse (F+H). For the quantification of the amount DSPP and HLA-A expression image J was used.
Figure 8:
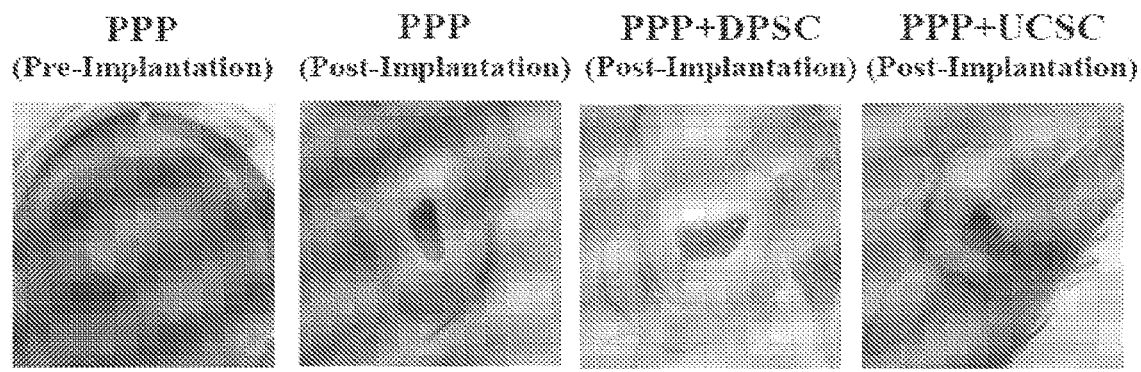
Figure 8:
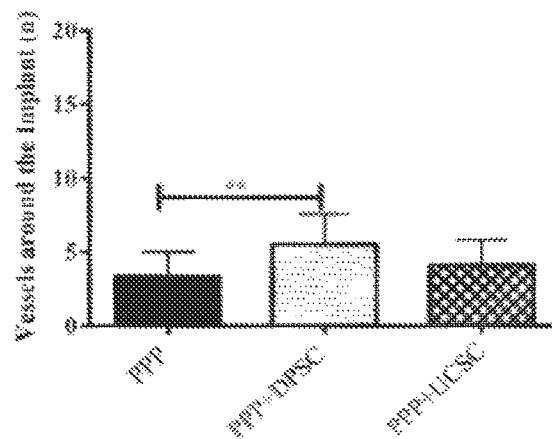
Figure 8:
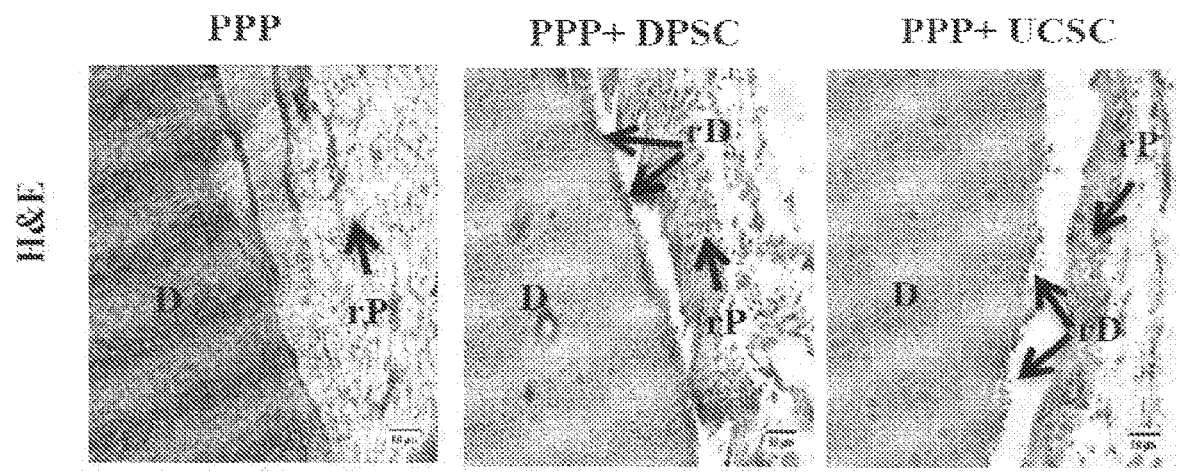
Figure 8:
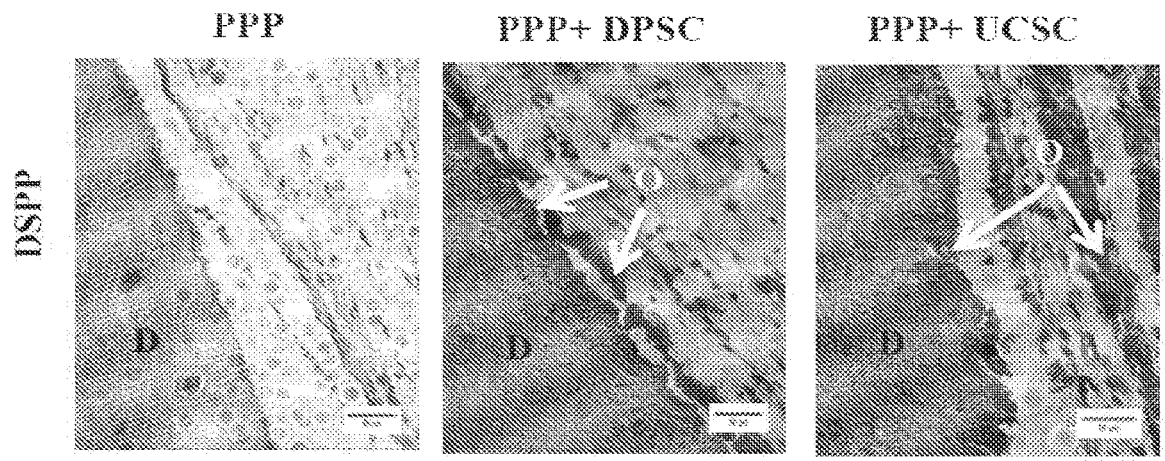
Figure 8:
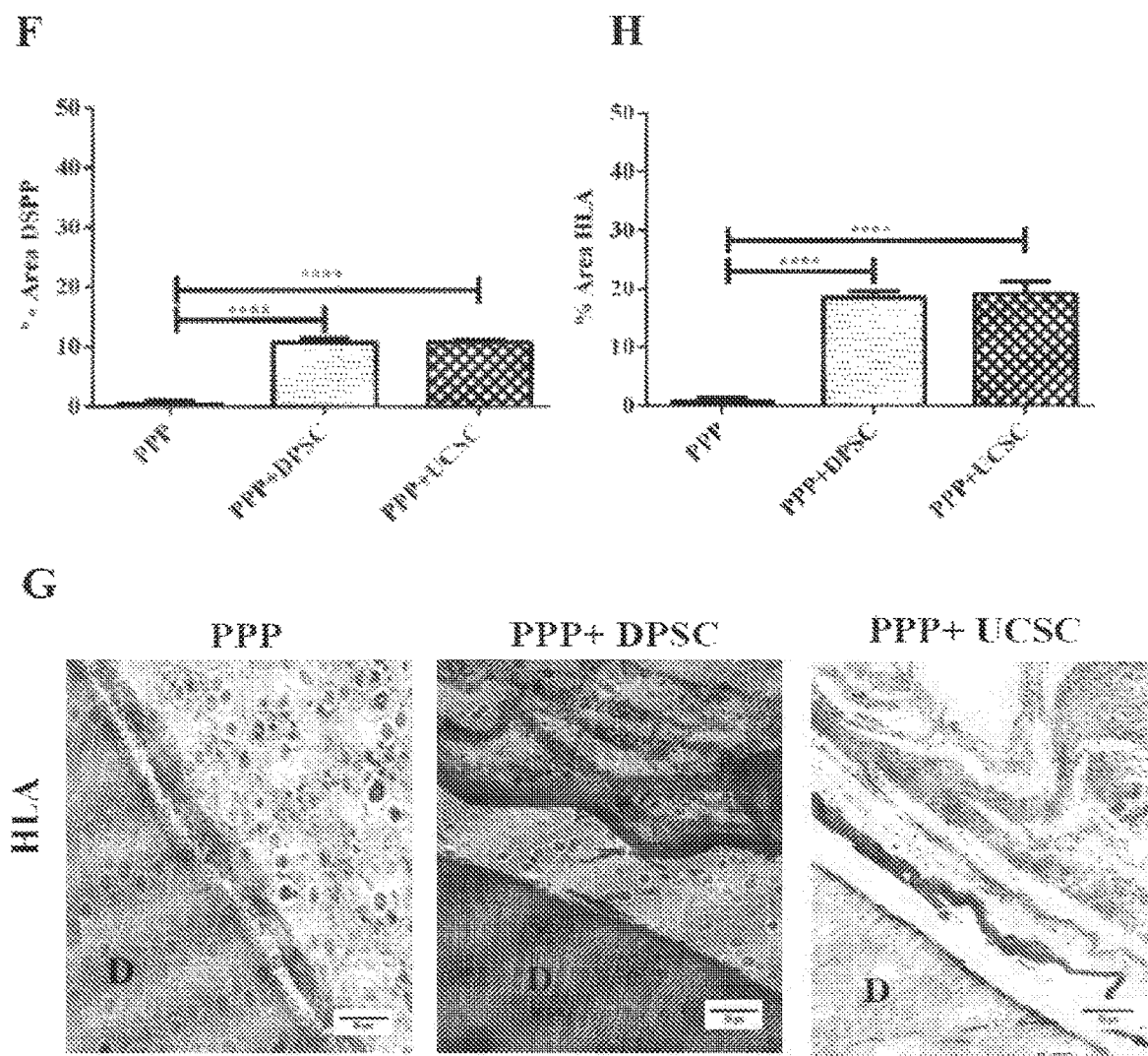

Example 25. In Vivo Implantation of Dentin-Disc/PPP Scaffold and Evaluation of Dentin and Angiogenic Formation The dentin-discs/PPP scaffolds were implanted subcutaneously for 30 days (FIG. 8A). Images were taken of the implants prior removal (FIG. 8B) and an evaluation of the vessel formation around the dentin dentin-discs/PPP was performed with image J. The results have shown a 1.6 fold increase ($P\leq0.01$) in vessels formation around the dentin-disc for the PPP+DPSC compared to PPP alone (FIG. 8C). After imaging, the dentin-discs/PPP scaffolds were removed, decalcified and processed for histology. The hematoxylin and eosin results (FIG. 8D) have shown that DPSC or UC-MSC were well incorporated in the PPP and migrated towards the dentin wall forming a dense layer of new mineralized dentin-like tissue Immunohistochemical staining as shown in FIG. 8E revealed a positive staining for dentin sialoprotien (DSPP) which implies the formation of new dentin and odontoblast formation for both DPSC and UC-MSC. To quantify, the amount of DSPP expression image J was used. The results have shown a 28.1 fold change ($P\leq0.0001$) increase for PPP+DPSC compared to PPP alone and 28.5 fold change ($P\leq0.0001$) difference for PPP+UC-MSC compared to PPP (FIG. 8F). Human leukocyte antigen (HLA) was used to confirm the presence of human cells. As shown in FIG. 8G, the majority of the cells stained positively for the antibody confirming the human cell origin of these cells. Image J analysis revealed an increase in the HLA expression for PPP+DPSC (24.6 fold change) and PPP+UC-MSC (25.5 fold change) ($P\leq0.0001$). The results have shown an increase for PPP+DPSC compared to PPP alone ($P\leq1.0001$) and also a difference for PPP+UC-MSC compared to PPP alone ($P\leq0.0001$) for both DSPP and HLA-A markers (FIG. 8H).

The invention claimed is:

1. A method for regenerating pulp tissue in a root canal, comprising inserting a composition comprising a population of multipotent stromal cells encapsulated in Platelet-Poor Plasma (PPP) into the root canal.

2. The method according to claim 1, wherein the population of multipotent stromal cells is selected from the group consisting of: dental pulp stem cells (DPSCs), stem cells from exfoliated deciduous teeth (SHED), periodontal ligament stem cells (PDLSCs), stem cells from apical papilla (SCAP), dental follicle progenitor cells (DFPCs), Placental MSCs (P-MSCs), bone marrow MSCs (mesenchymal stem cells), adipose tissue derived MSCs and umbilical cord blood (UC-MSCs).

3. The method according to claim 2, wherein the population of multipotent stromal cells is umbilical cord blood (UC-MSCs).

4. The method according to claim 1, wherein the method comprises pulpectomizing or enlarging and cleaning of a root canal infected with periapical disease; and injecting the composition into at least an apical area of the root canal.

5. The method according to claim 4, wherein a width of the root canal in the apical area is adjusted to a particular size, by enlargement of the root canal before injecting the composition into the apical area of the root canal.

6. The method of claim 1, wherein a concentration of the multipotent stromal cells in the composition ranges from $1\times10^3$ cells/$\mu$l to $1\times10^7$ cells/$\mu$l.

7. The method of claim 1, wherein a concentration of the multipotent stromal cells is in the composition is about $1\times10^6$ cells/$\mu$l.

* * * * *